United States Patent
Mitchell et al.

(10) Patent No.: US 12,239,811 B2
(45) Date of Patent: Mar. 4, 2025

(54) WIRELESS CHARGING, LOCALIZATION, AND DATA COMMUNICATION FOR IMPLANTABLE VASCULAR ACCESS DEVICES

(71) Applicant: Veris Health Inc., New York, NY (US)

(72) Inventors: James D. Mitchell, Walnut Creek, CA (US); Andrew A. Thoreson, Orono, MN (US); Theodore C. Johnson, Lake Forest Park, WA (US); Jayme Ormiston Coates, New Hartford, CT (US)

(73) Assignee: Veris Health Inc., New York, NY (US)

( * ) Notice: Subject to any disclaimer, the term of this patent is extended or adjusted under 35 U.S.C. 154(b) by 959 days.

(21) Appl. No.: 17/309,338

(22) PCT Filed: Nov. 20, 2019

(86) PCT No.: PCT/US2019/062350
§ 371 (c)(1),
(2) Date: May 19, 2021

(87) PCT Pub. No.: WO2020/106804
PCT Pub. Date: May 28, 2020

(65) Prior Publication Data
US 2021/0402164 A1 Dec. 30, 2021

Related U.S. Application Data

(60) Provisional application No. 62/769,698, filed on Nov. 20, 2018.

(51) Int. Cl.
*A61M 39/02* (2006.01)
*A61B 5/00* (2006.01)
(Continued)

(52) U.S. Cl.
CPC ....... *A61M 39/0208* (2013.01); *A61B 5/0031* (2013.01); *A61B 5/6865* (2013.01);
(Continued)

(58) Field of Classification Search
None
See application file for complete search history.

(56) References Cited

U.S. PATENT DOCUMENTS

| 4,834,720 A | 5/1989 | Blinkhorn |
| 4,846,191 A | 7/1989 | Brockway et al. |

(Continued)

FOREIGN PATENT DOCUMENTS

| AU | 691877 B2 | 5/1998 |
| CA | 2757836 C | 5/2017 |

(Continued)

OTHER PUBLICATIONS

Dubovitskaya, et al., "Secure and Trustable Electronic Medical Records Sharing using Blockchain", AMAI Annual Symposium Proceedings Achive, Jan. 1, 2017, pp. 650-659.
(Continued)

*Primary Examiner* — Raqiul A Choudhury

(57) ABSTRACT

An implantable vascular access device includes a fluid, a self-sealing cover disposed over the reservoir, and an outlet port configured to mate with a catheter, the outlet port fluidically coupled to the fluid reservoir. One or more sensors coupled to the device are configured to capture physiological data while the device is implanted within a patient. The device also includes a data communications unit configured to receive physiological data from the one or more sensors, obfuscate the physiological data, and transmit the obfuscated physiological data to one or more remote
(Continued)

computing devices. The device may also be inductively powered and/or can emit a localization signal in response to wireless interrogation.

17 Claims, 9 Drawing Sheets

(51) Int. Cl.
  *G06F 21/62* (2013.01)
  *G16H 10/60* (2018.01)
  *G16H 20/17* (2018.01)

(52) U.S. Cl.
  CPC ..... *A61M 39/0247* (2013.01); *G06F 21/6254* (2013.01); *G16H 10/60* (2018.01); *G16H 20/17* (2018.01); *A61M 2039/0238* (2013.01); *A61M 2039/0258* (2013.01); *A61M 2205/3324* (2013.01); *A61M 2205/3331* (2013.01); *A61M 2205/3507* (2013.01); *A61M 2205/3569* (2013.01); *A61M 2230/04* (2013.01); *A61M 2230/208* (2013.01); *A61M 2230/50* (2013.01)

(56) References Cited

U.S. PATENT DOCUMENTS

| | | |
|---|---|---|
| 4,861,341 A | 8/1989 | Woodburn |
| 4,929,236 A | 5/1990 | Sampson |
| 5,167,638 A | 12/1992 | Felix et al. |
| 5,185,003 A | 2/1993 | Brethauer |
| 5,281,205 A | 1/1994 | McPherson |
| 5,360,407 A | 11/1994 | Leonard et al. |
| 5,399,168 A | 3/1995 | Wadsworth et al. |
| 5,423,334 A | 6/1995 | Jordan |
| 5,476,460 A | 12/1995 | Montalvo |
| 5,558,641 A | 9/1996 | Glantz et al. |
| 5,613,945 A | 3/1997 | Cai et al. |
| 5,620,419 A | 4/1997 | Lui et al. |
| 5,637,102 A | 6/1997 | Tolkoff et al. |
| 5,743,873 A | 4/1998 | Cai et al. |
| 5,833,654 A | 11/1998 | Powers et al. |
| 5,951,512 A | 9/1999 | Dalton |
| 5,989,216 A | 11/1999 | Johnson et al. |
| 6,086,555 A | 7/2000 | Eliasen et al. |
| 6,113,572 A | 9/2000 | Gailey et al. |
| 6,213,973 B1 | 4/2001 | Eliasen et al. |
| 6,478,783 B1 | 11/2002 | Moorehead |
| 6,562,023 B1 | 5/2003 | Marrs et al. |
| 6,650,939 B2 | 11/2003 | Taepke et al. |
| 6,804,558 B2 | 10/2004 | Haller et al. |
| 6,847,844 B2 | 1/2005 | Sun et al. |
| 6,922,592 B2 | 7/2005 | Thompson et al. |
| 6,997,914 B2 | 2/2006 | Smith et al. |
| 7,037,273 B2 | 5/2006 | Zhu et al. |
| 7,069,086 B2 | 6/2006 | Von |
| 7,070,591 B2 | 7/2006 | Adams et al. |
| 7,177,684 B1 | 2/2007 | Kroll et al. |
| 7,181,505 B2 | 2/2007 | Haller et al. |
| D546,440 S | 7/2007 | Burnside |
| D556,153 S | 11/2007 | Burnside |
| 7,324,949 B2 | 1/2008 | Bristol |
| 7,347,843 B2 | 3/2008 | Adams et al. |
| 7,351,233 B2 | 4/2008 | Parks |
| D574,950 S | 8/2008 | Zawacki et al. |
| 7,445,614 B2 | 11/2008 | Bunodiere et al. |
| 7,479,107 B2 | 1/2009 | Zhu et al. |
| 7,713,251 B2 | 5/2010 | Tallarida et al. |
| 7,762,999 B2 | 7/2010 | Byrum |
| 7,775,966 B2 | 8/2010 | Dlugos et al. |
| 7,785,302 B2 | 8/2010 | Powers |
| 7,831,301 B2 | 11/2010 | Webb et al. |
| 7,844,341 B2 | 11/2010 | Von et al. |
| 7,909,769 B2 | 3/2011 | Zhu et al. |
| 7,909,804 B2 | 3/2011 | Stats |
| 7,942,863 B2 | 5/2011 | Kalpin et al. |
| 7,947,022 B2 | 5/2011 | Amin et al. |
| 7,959,615 B2 | 6/2011 | Stats et al. |
| 7,972,314 B2 | 7/2011 | Bizup et al. |
| 8,025,639 B2 | 9/2011 | Powers et al. |
| 8,029,482 B2 | 10/2011 | Maniar et al. |
| 8,092,435 B2 | 1/2012 | Beling et al. |
| 8,140,160 B2 | 3/2012 | Pless et al. |
| 8,147,455 B2 | 4/2012 | Butts et al. |
| 8,175,694 B2 | 5/2012 | Webb et al. |
| 8,177,762 B2 | 5/2012 | Beasley et al. |
| 8,202,259 B2 | 6/2012 | Evans et al. |
| 8,301,254 B2 | 10/2012 | Mosesov et al. |
| D676,955 S | 2/2013 | Orome |
| 8,382,724 B2 | 2/2013 | Maniar et al. |
| 8,391,981 B2 | 3/2013 | Mosesov |
| 8,396,803 B1 | 3/2013 | Dala et al. |
| 8,401,659 B2 | 3/2013 | Von et al. |
| 8,409,221 B2 | 4/2013 | Franklin et al. |
| 8,439,835 B1 | 5/2013 | McKinley et al. |
| 8,475,417 B2 | 7/2013 | Powers et al. |
| 8,491,547 B2 | 7/2013 | Olsen et al. |
| 8,535,280 B2 | 9/2013 | Mitchell et al. |
| 8,535,281 B2 | 9/2013 | Travis et al. |
| 8,545,460 B2 | 10/2013 | Beasley et al. |
| 8,608,713 B2 | 12/2013 | Beasley et al. |
| 8,608,727 B2 | 12/2013 | Michels et al. |
| 8,615,305 B2 | 12/2013 | Von Arx et al. |
| 8,641,676 B2 | 2/2014 | Butts et al. |
| 8,641,688 B2 | 2/2014 | Powers et al. |
| 8,660,659 B2 | 2/2014 | Mosesov et al. |
| 8,744,581 B2 | 6/2014 | Mosesov |
| 8,805,478 B2 | 8/2014 | Powers et al. |
| 8,827,904 B2 | 9/2014 | Ball et al. |
| 8,920,389 B2 | 12/2014 | Kalpin et al. |
| 8,920,390 B2 | 12/2014 | Dalton et al. |
| 8,926,573 B2 | 1/2015 | Smith et al. |
| 8,932,271 B2 | 1/2015 | Hamatake et al. |
| 8,939,947 B2 | 1/2015 | Maniar et al. |
| 9,011,388 B2 | 4/2015 | Schwartz et al. |
| 9,017,256 B2 | 4/2015 | Gottesman |
| 9,072,881 B2 | 7/2015 | Dalton et al. |
| 9,079,004 B2 | 7/2015 | Wiley et al. |
| 9,101,264 B2 | 8/2015 | Acquista |
| 9,186,455 B2 | 11/2015 | Moyer |
| D748,249 S | 1/2016 | Pittet et al. |
| 9,248,268 B2 | 2/2016 | Wiley et al. |
| 9,327,106 B2 | 5/2016 | Beling et al. |
| 9,358,378 B2 | 6/2016 | Hanson et al. |
| 9,421,352 B2 | 8/2016 | Butts et al. |
| 9,474,888 B2 | 10/2016 | Wiley et al. |
| 9,485,883 B2 | 11/2016 | Koyama |
| 9,498,130 B2 | 11/2016 | Najafi et al. |
| 9,579,496 B2 | 2/2017 | Evans et al. |
| 9,603,992 B2 | 3/2017 | Powers |
| 9,603,993 B2 | 3/2017 | Powers |
| 9,642,556 B2 | 5/2017 | Mo et al. |
| 9,681,825 B2 | 6/2017 | Acquista |
| 9,717,895 B2 | 8/2017 | Wiley et al. |
| 9,814,833 B2 | 11/2017 | Kalpin |
| 9,821,150 B2 | 11/2017 | Pamment |
| 9,937,337 B2 | 4/2018 | Powers et al. |
| 9,950,150 B2 | 4/2018 | Beling et al. |
| 10,016,585 B2 | 7/2018 | Powers et al. |
| 10,022,094 B2 | 7/2018 | Kerr et al. |
| 10,052,470 B2 | 8/2018 | Powers et al. |
| 10,052,471 B2 | 8/2018 | Hamatake et al. |
| 10,086,186 B2 | 10/2018 | Evans et al. |
| 10,155,101 B2 | 12/2018 | Wiley et al. |
| 10,207,095 B2 | 2/2019 | Barron et al. |
| 10,307,581 B2 | 6/2019 | Hibdon et al. |
| 10,321,292 B2 | 6/2019 | Pflugh et al. |
| 11,096,582 B2 | 8/2021 | Mitchell et al. |
| 2001/0027331 A1 | 10/2001 | Thompson |
| 2002/0052539 A1 | 5/2002 | Haller et al. |
| 2002/0193846 A1 | 12/2002 | Pool et al. |
| 2003/0014091 A1 | 1/2003 | Rastegar et al. |
| 2003/0076369 A1* | 4/2003 | Resner .......... H04L 69/329 709/217 |

(56) References Cited

U.S. PATENT DOCUMENTS

| | | |
|---|---|---|
| 2004/0054352 A1 | 3/2004 | Adams et al. |
| 2005/0124980 A1 | 6/2005 | Sanders |
| 2006/0116648 A1 | 6/2006 | Hamatake |
| 2006/0178617 A1 | 8/2006 | Adams et al. |
| 2006/0178648 A1 | 8/2006 | Barron et al. |
| 2007/0016089 A1 | 1/2007 | Fischell et al. |
| 2007/0078391 A1 | 4/2007 | Wortley et al. |
| 2007/0135765 A1 | 6/2007 | Miller et al. |
| 2007/0270672 A1 | 11/2007 | Hayter |
| 2008/0114308 A1 | 5/2008 | Di et al. |
| 2009/0118683 A1 | 5/2009 | Hanson et al. |
| 2009/0227951 A1 | 9/2009 | Powers et al. |
| 2010/0191166 A1 | 7/2010 | Phillips et al. |
| 2010/0274221 A1 | 10/2010 | Sigg et al. |
| 2010/0286467 A1* | 11/2010 | Pesach ............... A61M 5/158 604/257 |
| 2011/0137134 A1* | 6/2011 | Hemmerling ........ A61B 5/4821 600/301 |
| 2011/0184342 A1 | 7/2011 | Pesach et al. |
| 2011/0202041 A1 | 8/2011 | Forsell |
| 2012/0172711 A1 | 7/2012 | Kerr et al. |
| 2012/0245439 A1 | 9/2012 | Andre et al. |
| 2013/0150811 A1 | 6/2013 | Horgan |
| 2014/0088519 A1 | 3/2014 | Kerr |
| 2014/0142518 A1* | 5/2014 | Nardone ............... A61M 39/02 604/244 |
| 2014/0207086 A1 | 7/2014 | Stats et al. |
| 2014/0236105 A1 | 8/2014 | Hanson et al. |
| 2014/0249503 A1 | 9/2014 | Bennett et al. |
| 2015/0005738 A1* | 1/2015 | Blacker ............... A61B 34/30 604/95.01 |
| 2015/0025478 A1 | 1/2015 | Hibdon et al. |
| 2015/0112315 A1 | 4/2015 | Cudak et al. |
| 2016/0317797 A1 | 11/2016 | Smith et al. |
| 2017/0028185 A1 | 2/2017 | Wiley et al. |
| 2017/0316162 A1* | 11/2017 | Wall Warner ........ H04L 9/0637 |
| 2017/0340872 A1 | 11/2017 | Hanson et al. |
| 2018/0043149 A1 | 2/2018 | Martin |
| 2018/0078751 A1 | 3/2018 | Fedor et al. |
| 2018/0103859 A1 | 4/2018 | Provenzano |
| 2018/0113984 A1* | 4/2018 | Doshi ............... G16H 20/40 |
| 2018/0147343 A1 | 5/2018 | Tyson |
| 2018/0161565 A1 | 6/2018 | Maniar et al. |
| 2018/0177982 A1 | 6/2018 | Albany et al. |
| 2018/0193626 A1 | 7/2018 | Beling et al. |
| 2018/0263511 A1 | 9/2018 | Burnes et al. |
| 2018/0333058 A1* | 11/2018 | Coulon ............... A61B 5/0022 |
| 2019/0054284 A1 | 2/2019 | Smith et al. |
| 2020/0155003 A1 | 5/2020 | Mitchell et al. |
| 2020/0179669 A1 | 6/2020 | Mitchell et al. |
| 2021/0361166 A1 | 11/2021 | Mitchell et al. |
| 2022/0015708 A1 | 1/2022 | Mitchell et al. |

FOREIGN PATENT DOCUMENTS

| | | |
|---|---|---|
| CN | 104740765 B | 3/2017 |
| DE | 102011078711 A1 | 1/2013 |
| EP | 0392199 A1 | 10/1990 |
| EP | 1391218 A3 | 4/2004 |
| EP | 1413329 B1 | 12/2005 |
| EP | 1773448 A1 | 4/2007 |
| EP | 1962921 A2 | 9/2008 |
| EP | 2020945 B1 | 2/2013 |
| EP | 2859911 A1 | 4/2015 |
| EP | 1874393 B1 | 9/2017 |
| EP | 2416828 B1 | 2/2018 |
| EP | 2501294 B1 | 8/2018 |
| ES | 2041000 T3 | 11/1993 |
| ES | 2041461 T3 | 11/1993 |
| ES | 2136613 T3 | 12/1999 |
| JP | 2000513952 A | 10/2000 |
| JP | 4795523 B2 | 11/2000 |
| JP | 2005169113 A | 6/2005 |
| JP | 4947876 B2 | 3/2012 |
| JP | 2016504158 A | 2/2016 |
| WO | 9934859 A1 | 7/1999 |
| WO | 2010118144 A1 | 10/2010 |
| WO | 2015097255 A2 | 7/2015 |
| WO | 2018/217633 A1 | 11/2018 |
| WO | 2019118929 A1 | 6/2019 |
| WO | 2020/106890 A1 | 5/2020 |
| WO | 2020106804 A1 | 5/2020 |
| WO | 2020106842 A1 | 5/2020 |
| WO | 2021102467 | 5/2021 |
| WO | 2022/140766 A1 | 6/2022 |

OTHER PUBLICATIONS

International Search Report and Written Opinion mailed Feb. 24, 2020; International Application No. PCT/US2019/062350; 14 pages.

Kuo et al., "Blockcain distributed ledger technologies for biomedical and health care applications", Journal of the American Medical Informatics Association, vol. 24, No. 6, Sep. 8, 2017, pp. 1211-1220.

* cited by examiner

WIRELESS CHARGING, LOCALIZATION, AND DATA COMMUNICATION FOR IMPLANTABLE VASCULAR ACCESS DEVICES

CROSS-REFERENCE TO RELATED APPLICATION

The present application is a 371 U.S. national phase application of International Patent Application No. PCT/US2019/062350, filed Nov. 20, 2019, which claims priority to U.S. Provisional Patent Application No. 62/769,698, filed Nov. 20, 2018, each of which are incorporated by reference herein in its entirety.

TECHNICAL FIELD

The present technology relates to implantable medical devices and associated systems and methods of use. In particular, the present technology is directed to devices for wireless charging, localization, and data communications for implantable medical devices such as vascular access devices.

BACKGROUND

Implantable devices are used in the field of medicine for many diagnostic and therapeutic purposes. With the advent of advanced technology such as miniaturization of electronic components, advanced prototyping and manufacturing techniques, and data storage and analytics, the field of implantable medical devices has grown substantially. This field includes devices such as pacemakers, implantable cardioverter/defibrillators (ICD), deep brain stimulators, insulin pumps, orthopedic devices, and monitoring devices such as pulmonary artery pressure monitors.

Within the field of implanted medical devices are vascular access devices (e.g., vascular access ports). These devices are frequently used in patients that require repeated intravenous infusion of medication as they provide a permanent and sterile means of vascular access, obviating the need to place an intravenous catheter during each medication infusion. The most common use of vascular access devices is for chemotherapy administration in cancer patients, but such devices are useful in other conditions as well. For example, patients who require long term and repeated intravenous antibiotic medication such as for treatment of cystic fibrosis can benefit from an implantable vascular access device. Similarly, vascular access devices may be used in patients with rheumatologic disorders like lupus or rheumatoid arthritis who require immunosuppression medication infusions. Vascular access devices typically include a reservoir attached to a catheter. The entire unit is placed completely within a patient's body using a minimally invasive surgical procedure. In most cases the reservoir is placed in a small pocket created in the upper chest wall just inferior to the clavicle, and the catheter is inserted into the internal jugular vein or the subclavian vein with the tip resting in the superior vena cava or the right atrium. However, vascular access devices can be placed in other parts of the body and/or with the catheter positioned in alternative sites as well. In conventional devices, the reservoir is typically bulky such that the overlying skin protrudes, allowing a clinician to use palpation to localize the device for access when it is to be used for a medication infusion or aspiration of blood for testing. A self-sealing cover (e.g., a thick silicone membrane) is disposed over and seals the reservoir, allowing for repeated access using a non-coring (e.g., Huber type) needle that is inserted through the skin and into the port. This access procedure establishes a system in which there is fluid communication between the needle, the vascular access device, the catheter, and the vascular space, thereby enabling infusion of medication or aspiration of blood via a transcutaneous needle.

SUMMARY

The present technology is directed to vascular access devices and mechanisms for localization, wireless charging, and/or data communication for such devices. The subject technology is illustrated, for example, according to various aspects described below, including with reference to FIGS. 1-9B. Various examples of aspects of the subject technology are described as numbered clauses (1, 2, 3, etc.) for convenience. These are provided as examples and do not limit the subject technology.

Clause 1. An implantable vascular access device comprising: a fluid reservoir; a self-sealing cover disposed over the reservoir; an outlet port configured to mate with a catheter, the outlet port fluidically coupled to the fluid reservoir; one or more sensors configured to capture physiological data while the device is implanted within a patient; and a data communications unit configured to: receive physiological data from the one or more sensors; obfuscate the physiological data; and transmit the obfuscated physiological data to one or more remote computing devices.

Clause 2. The device of any one of the preceding clauses, wherein obfuscating the physiological data comprises: encrypting the physiological data; and parsing the encrypted physiological data into component packets.

Clause 3. The device of any one of the preceding clauses, wherein the component packets are individually unintelligible.

Clause 4. The device of any one of the preceding clauses, wherein encrypting the physiological data comprises one or more of: symmetric-key encryption or asymmetric-key encryption.

Clause 5. The device of any one of the preceding clauses, wherein obfuscating the physiological data further comprises arranging the component packets into a data stream interspersed with filler packets containing non-physiological data, and wherein transmitting the obfuscated physiological data comprises transmitting the data stream to one or more remote computing devices.

Clause 6. The device of any one of the preceding clauses, wherein the filler packets have a predetermined data size.

Clause 7. The device of any one of the preceding clauses, wherein the filler packets are interspersed into the data stream according to a predetermined pattern.

Clause 8. The device of any one of the preceding clauses, wherein obfuscating the physiological data further comprises: after parsing the encrypted data into component packets, re-ordering the component packets; and arranging the re-ordered component packets into a data stream, wherein transmitting the obfuscated physiological data comprises transmitting the data stream to one or more remote computing devices.

Clause 9. The device of any one of the preceding clauses, wherein transmitting the obfuscated physiological data to one or more remote computing devices comprises transmitting a first packet at a first time and, after a predetermined time delay, transmitting a second packet at a second time.

Clause 10. The device of any one of the preceding clauses, wherein the predetermined time delay is at least 60 seconds.

Clause 11. The device of any one of the preceding clauses, wherein the predetermined time delay is at least 10 minutes.

Clause 12. The device of any one of the preceding clauses, wherein the predetermined time delay is at least one hour.

Clause 13. The device of any one of the preceding clauses, wherein the predetermined time delay corresponds to a predetermined pattern for transmission of subsequent packets.

Clause 14. The device of any one of the preceding clauses, wherein the data communications unit is configured to transmit a first of the packets to a first remote computing device and to transmit a second of the packets to a second remote computing device, different from the first remote computing device.

Clause 15. The device of any one of the preceding clauses, wherein the data communications unit is configured to: obfuscate the physiological data according to a first technique; transmit the obfuscated physiological data to one or more remote computing devices; receive a response from the one or more remote computing devices; receive additional physiological data from the one or more sensors; and based on the response from the one or more remote computing devices, obfuscate the physiological data according to a second technique, different from the first technique.

Clause 16. The device of any one of the preceding clauses, wherein the one or more remote computing devices is associated with a blockchain network.

Clause 17. The device of any one of the preceding clauses, wherein the data communications unit is configured to transmit the obfuscated physiological data to one or more remote computing devices via short-range wireless transmission.

Clause 18. The device of any one of the preceding clauses, wherein the short-range wireless transmission comprises one or more of: near-field communication (NFC), infrared wireless, Bluetooth, ZigBee, Wi-Fi, inductive coupling, or capacitive coupling.

Clause 19. The device of any one of the preceding clauses, further comprising a conductive coil, wherein transmitting the obfuscated physiological data to one or more remote computing devices comprises: encoding the obfuscated physiological data via frequency modulation and/or amplitude modulation; and driving the conductive coil with electrical energy corresponding to the encoded data, thereby transmitting the encoded data to an inductively coupled remote computing device.

Clause 20. The device of any one of the preceding clauses, wherein the sensors comprise one or more of: EKG sensors, a temperature sensor, an accelerometer, a gyroscope, a magnetometer, a pulse oximeter, a pressure sensor, a light sensor, a pH sensor, a blood-gas sensor, or a blood-chemistry sensor.

Clause 21. The device of any one of the preceding clauses, wherein the physiological data comprises one or more of: an EKG reading, a pulse rate, a blood pressure, a temperature, detected-motion data, a blood oxygenation, pH data, or blood-constituent data.

Clause 22. The device of any one of the preceding clauses, further comprising a catheter fluidically coupled to the output port.

Clause 23. An implantable medical device comprising: a biocompatible body; one or more sensors coupled to the device body, the sensors configured to capture physiological data while the device is implanted within a patient; and a data communications unit configured to: receive physiological data from the one or more sensors; obfuscate the physiological data; and transmit the obfuscated physiological data to one or more remote computing devices.

Clause 24. The device of any one of the preceding clauses, wherein obfuscating the physiological data comprises: encrypting the physiological data; and parsing the encrypted physiological data into component packets.

Clause 25. The device of any one of the preceding clauses, wherein the component packets are individually unintelligible.

Clause 26. The device of any one of the preceding clauses, wherein encrypting the physiological data comprises one or more of: symmetric-key encryption or asymmetric-key encryption.

Clause 27. The device of any one of the preceding clauses, wherein obfuscating the physiological data further comprises arranging the component packets into a data stream interspersed with filler packets containing non-physiological data, and wherein transmitting the obfuscated physiological data comprises transmitting the data stream to one or more remote computing devices.

Clause 28. The device of any one of the preceding clauses, wherein the filler packets have a predetermined data size.

Clause 29. The device of any one of the preceding clauses, wherein the filler packets are interspersed into the data stream according to a predetermined pattern.

Clause 30. The device of any one of the preceding clauses, wherein obfuscating the physiological data further comprises: after parsing the encrypted data into component packets, re-ordering the component packets; and arranging the re-ordered component packets into a data stream, wherein transmitting the obfuscated physiological data comprises transmitting the data stream to one or more remote computing devices.

Clause 31. The device of any one of the preceding clauses, wherein transmitting the obfuscated physiological data to one or more remote computing devices comprises transmitting a first packet at a first time and, after a predetermined time delay, transmitting a second packet at a second time.

Clause 32. The device of any one of the preceding clauses, wherein the predetermined time delay is at least 60 seconds.

Clause 33. The device of any one of the preceding clauses, wherein the predetermined time delay is at least 10 minutes.

Clause 34. The device of any one of the preceding clauses, wherein the predetermined time delay is at least one hour.

Clause 35. The device of any one of the preceding clauses, wherein the predetermined time delay corresponds to a predetermined pattern for transmission of subsequent packets.

Clause 36. The device of any one of the preceding clauses, wherein the data communications unit is configured to transmit a first of the packets to a first remote computing device and to transmit a second of the packets to a second remote computing device, different from the first remote computing device.

Clause 37. The device of any one of the preceding clauses, wherein the data communications unit is configured to: obfuscate the physiological data according to a first technique; transmit the obfuscated physiological data to one or more remote computing devices; receive a response from the one or more remote computing devices; receive additional physiological data from the one or more sensors; and based on the response from the one or more remote computing devices, obfuscate the physiological data according to a second technique, different from the first technique.

Clause 38. The device of any one of the preceding clauses, wherein the one or more remote computing devices is associated with a blockchain network.

Clause 39. The device of any one of the preceding clauses, wherein the data communications unit is configured to transmit the obfuscated physiological data to one or more remote computing devices via short-range wireless transmission.

Clause 40. The device of any one of the preceding clauses, wherein the short-range wireless transmission comprises one or more of: near-field communication (NFC), infrared wireless, Bluetooth, ZigBee, Wi-Fi, inductive coupling, or capacitive coupling.

Clause 41. The device of any one of the preceding clauses, further comprising a conductive coil, wherein transmitting the obfuscated physiological data to one or more remote computing devices comprises: encoding the obfuscated physiological data via frequency modulation and/or amplitude modulation; and driving the conductive coil with electrical energy corresponding to the encoded data, thereby transmitting the encoded data to an inductively coupled remote computing device.

Clause 42. The device of any one of the preceding clauses, wherein the sensors comprise one or more of: EKG sensors, a temperature sensor, an accelerometer, a gyroscope, a magnetometer, a pulse oximeter, a pressure sensor, a light sensor, a pH sensor, a blood-gas sensor, or a blood-chemistry sensor.

Clause 43. The device of any one of the preceding clauses, wherein the physiological data comprises one or more of: an EKG reading, a pulse rate, a blood pressure, a temperature, detected-motion data, a blood oxygenation, pH data, or blood-constituent data.

Clause 44. The device of any one of the preceding clauses, further comprising a catheter fluidically coupled to an output port of the body.

Clause 45. A method for communicating patient data between an implantable vascular access device and one or more remote computing devices, the method comprising: capturing physiological data from one or more sensors of the implantable vascular access device while implanted within a patient; obfuscating, via the implantable vascular access device, the physiological data; and transmitting, via the implantable vascular access device, the obfuscated physiological data to one or more remote computing devices.

Clause 46. The method of any one of the preceding clauses, wherein obfuscating the physiological data comprises: encrypting the physiological data; and parsing the encrypted physiological data into component packets.

Clause 47. The method of any one of the preceding clauses, wherein the component packets are individually unintelligible.

Clause 48. The method of any one of the preceding clauses, wherein encrypting the physiological data comprises one or more of: symmetric-key encryption or asymmetric-key encryption.

Clause 49. The method of any one of the preceding clauses, wherein obfuscating the physiological data further comprises arranging the component packets into a data stream interspersed with filler packets containing non-physiological data, and wherein transmitting the obfuscated physiological data comprises transmitting the data stream to one or more remote computing devices.

Clause 50. The method of any one of the preceding clauses, wherein the filler packets have a predetermined data size.

Clause 51. The method of any one of the preceding clauses, wherein the filler packets are interspersed into the data stream according to a predetermined pattern.

Clause 52. The method of any one of the preceding clauses, wherein obfuscating the physiological data further comprises: after parsing the encrypted data into component packets, re-ordering the component packets; and arranging the re-ordered component packets into a data stream, wherein transmitting the obfuscated physiological data comprises transmitting the data stream to one or more remote computing devices.

Clause 53. The method of any one of the preceding clauses, wherein transmitting the obfuscated physiological data to one or more remote computing devices comprises transmitting a first packet at a first time and, after a predetermined time delay, transmitting a second packet at a second time.

Clause 54. The method of any one of the preceding clauses, wherein the predetermined time delay is at least 60 seconds.

Clause 55. The method of any one of the preceding clauses, wherein the predetermined time delay is at least 10 minutes.

Clause 56. The method of any one of the preceding clauses, wherein the predetermined time delay is at least one hour.

Clause 57. The method of any one of the preceding clauses, wherein the predetermined time delay corresponds to a predetermined pattern for transmission of subsequent packets.

Clause 58. The method of any one of the preceding clauses, wherein the data communications unit is configured to transmit a first of the packets to a first remote computing device and to transmit a second of the packets to a second remote computing device, different from the first remote computing device.

Clause 59. The method of any one of the preceding clauses, wherein the obfuscating comprises obfuscating the physiological data according to a first technique, the method further comprising: receiving a response from the one or more remote computing devices; capturing additional physiological data from the one or more sensors; and based on the response from the one or more remote computing devices, obfuscating the physiological data according to a second technique, different from the first technique.

Clause 60. The method of any one of the preceding clauses, wherein the one or more remote computing devices is associated with a blockchain network.

Clause 61. The method of any one of the preceding clauses, wherein the transmitting comprises transmitting the obfuscated physiological data to one or more remote computing devices via short-range wireless transmission.

Clause 62. The method of any one of the preceding clauses, wherein the short-range wireless transmission comprises one or more of: near-field communication (NFC), infrared wireless, Bluetooth, ZigBee, Wi-Fi, inductive coupling, or capacitive coupling.

Clause 63. The method of any one of the preceding clauses, further comprising a conductive coil, wherein transmitting the obfuscated physiological data to one or more remote computing devices comprises: encoding the obfuscated physiological data via frequency modulation and/or amplitude modulation; and driving the conductive coil with electrical energy corresponding to the encoded data, thereby transmitting the encoded data to an inductively coupled remote computing device.

Clause 64. The method of any one of the preceding clauses, wherein the sensors comprise one or more of: EKG sensors, a temperature sensor, an accelerometer, a gyroscope, a magnetometer, a pulse oximeter, a pressure sensor, a light sensor, a pH sensor, a blood-gas sensor, or a blood-chemistry sensor.

Clause 65. The method of any one of the preceding clauses, wherein the physiological data comprises one or more of: an EKG reading, a pulse rate, a blood pressure, a temperature, detected-motion data, a blood oxygenation, pH data, or blood-constituent data.

Clause 66. The method of any one of the preceding clauses, further comprising fluidically coupling a catheter to the output port.

Clause 67. A method for communicating patient data between an implantable vascular access device and one or more remote computing devices, the method comprising: receiving, from an implantable vascular access device, obfuscated physiological data based on physiological data obtained via sensors of the implantable vascular access device; and de-obfuscating the obfuscated physiological data.

Clause 68. The method of any one of the preceding clauses, wherein de-obfuscating the physiological data comprises: re-assembling component packets of data; and decrypting the component packets of physiological data.

Clause 69. The method of any one of the preceding clauses, wherein the component packets are individually unintelligible.

Clause 70. The method of any one of the preceding clauses, wherein decrypting the component packets of physiological data comprises one or more of: symmetric-key encryption or asymmetric-key encryption.

Clause 71. The method of any one of the preceding clauses, wherein re-assembling the component packets further comprises re-arranging the component packets and removing interspersed filter packets containing non-physiological data.

Clause 72. The method of any one of the preceding clauses, wherein the filler packets have a predetermined data size.

Clause 73. The method of any one of the preceding clauses, wherein the filler packets are interspersed into a data stream according to a predetermined pattern.

Clause 74. The method of any one of the preceding clauses, wherein re-assembling the component packets comprises receiving a first packet at a first time and, after a predetermined time delay, receiving a second packet at a second time.

Clause 75. The method of any one of the preceding clauses, wherein the predetermined time delay is at least 60 seconds.

Clause 76. The method of any one of the preceding clauses, wherein the predetermined time delay is at least 10 minutes.

Clause 77. The method of any one of the preceding clauses, wherein the predetermined time delay is at least one hour.

Clause 78. The method of any one of the preceding clauses, wherein the predetermined time delay corresponds to a predetermined pattern for reception of subsequent packets.

Clause 79. The method of any one of the preceding clauses, wherein the de-obfuscating comprises de-obfuscating the physiological data according to a first technique, the method further comprising: transmitting a response to the implantable vascular access device; receiving additional obfuscated physiological data from the implantable vascular access device; and de-obfuscating the additional obfuscated physiological data according to a second technique, different from the first technique.

Clause 80. The method of any one of the preceding clauses, wherein the receiving comprises receiving the obfuscated physiological data via short-range wireless transmission.

Clause 81. The method of any one of the preceding clauses, wherein the short-range wireless transmission comprises one or more of: near-field communication (NFC), infrared wireless, Bluetooth, ZigBee, Wi-Fi, inductive coupling, or capacitive coupling.

Clause 82. The method of any one of the preceding clauses, further comprising a conductive coil, wherein receiving the obfuscated physiological data comprises reading a current induced in the conductive coil via the implantable vascular access device, wherein the obfuscated physiological data is encoded into the current via frequency modulation and/or amplitude modulation.

Clause 83. The method of any one of the preceding clauses, wherein the physiological data comprises one or more of: an EKG reading, a pulse rate, a blood pressure, a temperature, detected-motion data, a blood oxygenation, pH data, or blood-constituent data.

Clause 84. An implantable vascular access device comprising: a fluid reservoir; a self-sealing cover disposed over the reservoir; an outlet port configured to mate with a catheter, the outlet port fluidically coupled to the fluid reservoir; an antenna configured to inductively couple with an interrogation device; a localization unit electrically coupled to the antenna, the localization unit configured to emit a localization signal in response to electrical energy received from the antenna, the localization signal configured to aid identification of the device position while implanted within a patient.

Clause 85. The device of any one of the preceding clauses, wherein the device does not include a battery.

Clause 86. The device of any one of the preceding clauses, wherein the localization unit is configured to emit the localization signal only while the antenna is inductively coupled with the interrogation device.

Clause 87. The device of any one of the preceding clauses, wherein the device comprises a rechargeable battery, and wherein the antenna is electrically coupled to the battery such that, in the presence of the interrogation device, electrical energy is delivered to the battery.

Clause 88. The device of any one of the preceding clauses, wherein the localization unit comprises a light source, and wherein the localization signal comprises light emitted from the light source.

Clause 89. The device of any one of the preceding clauses, wherein the localization unit comprises a plurality of light sources disposed around a periphery of the self-sealing cover.

Clause 90. The device of any one of the preceding clauses, wherein the light source is configured to emit light that transilluminates the patient's skin when the device is implanted subcutaneously.

Clause 91. The device of any one of the preceding clauses, wherein the localization unit comprises a speaker, and wherein the localization signal comprises sound emitted from the speaker.

Clause 92. The device of any one of the preceding clauses, wherein the localization unit comprises a conductive coil, and wherein the localization signal comprises a magnetic field induced by the coil.

Clause 93. The device of any one of the preceding clauses, wherein the localization unit comprises one or more stationary magnets, and wherein the localization signal comprises a magnetic field produced by the one or more stationary magnets.

Clause 94. The device of any one of the preceding clauses, wherein the localization unit comprises a radio frequency emitter and wherein the localization signal comprises a radio frequency signal emitted.

Clause 95. The device of any one of the preceding clauses, wherein the localization unit comprises an actuator, and wherein the localization signal comprises movement or vibration via the actuator.

Clause 96. The device of any one of the preceding clauses, wherein the localization unit comprises an actuator, and wherein the localization signal comprises protrusions rising from a surface of the device.

Clause 97. The device of any one of the preceding clauses, wherein the localization unit comprises a radioisotope, and wherein the localization signal comprises electromagnetic radiation emitted from the radioisotope Clause 98. The device of any one of the preceding clauses, wherein the localization unit comprises an ultrasound transducer, and wherein the localization signal comprises an ultrasound beam emitted from the ultrasound transducer.

Clause 99. The device of any one of the preceding clauses, wherein the localization unit comprises a heating element, and wherein the localization signal comprises an increased temperature of the heating element.

Clause 100. The device of any one of the preceding clauses, wherein the localization signal comprises patient data transmitted to the interrogation device.

Clause 101. The device of any one of the preceding clauses, further comprising one or more sensors configured to capture physiological data, and wherein the patient data comprises the captured physiological data.

Clause 102. The device of any one of the preceding clauses, wherein the sensors comprise one or more of: EKG sensors, a temperature sensor, an accelerometer, a gyroscope, a magnetometer, a pulse oximeter, a pressure sensor, a light sensor, a pH sensor, a blood-gas sensor, or a blood-chemistry sensor.

Clause 103. The device of any one of the preceding clauses, wherein the physiological data comprises one or more of: an EKG reading, a pulse rate, a blood pressure, a temperature, detected-motion data, a blood oxygenation, pH data, or blood-constituent data.

Clause 104. The device of any one of the preceding clauses, further comprising a catheter fluidically coupled to the output port.

Clause 105. The device of any one of the preceding clauses, wherein the localization unit is further configured to: detect a characteristic of the inductively coupled interrogation device; and based on the characteristic, terminate or preclude emission of the localization signal.

Clause 106. The device of any one of the preceding clauses, wherein the localization unit is further configured to: preclude emission of the localization signal if the characteristic indicates unsuitability for pairing with the interrogation device; and allow emission of the localization signal if the characteristic indicates suitability for pairing with the interrogation device.

Clause 107. The device of any one of the preceding clauses, wherein the characteristic is a field intensity threshold of the electrical energy received from the interrogation device Clause 108. The device of any one of the preceding clauses, wherein the characteristic is a frequency of the electrical energy received from the interrogation device.

Clause 109. The device of any one of the preceding clauses, wherein the characteristic is a frequency sequence of the electrical energy received from the interrogation device.

Clause 110. An implantable medical device comprising: a biocompatible housing; an electrically conductive coil received within the housing and configured to inductively couple with an interrogation device; a localization unit within the housing, the localization unit electrically coupled to the coil and configured to emit a localization signal in response to electrical energy received from the coil.

Clause 111. The device of any one of the preceding clauses, wherein the device does not include a battery.

Clause 112. The device of any one of the preceding clauses, wherein the localization unit is configured to emit the localization signal only while the coil is inductively coupled with the interrogation device.

Clause 113. The device of any one of the preceding clauses, wherein the device comprises a rechargeable battery, and wherein the coil is electrically coupled to the battery such that, in the presence of the interrogation device, electrical energy is delivered to the battery.

Clause 114. The device of any one of the preceding clauses, wherein the localization unit comprises a light source, and wherein the localization signal comprises light emitted from the light source.

Clause 115. The device of any one of the preceding clauses, wherein the localization unit comprises a plurality of light sources disposed on the housing.

Clause 116. The device of any one of the preceding clauses, wherein the light source is configured to emit light that transilluminates a patient's skin when the device is implanted subcutaneously.

Clause 117. The device of any one of the preceding clauses, wherein the localization unit comprises a speaker, and wherein the localization signal comprises sound emitted from the speaker.

Clause 118. The device of any one of the preceding clauses, wherein the localization unit comprises a conductive coil, and wherein the localization signal comprises a magnetic field induced by the coil.

Clause 119. The device of any one of the preceding clauses, wherein the localization unit comprises one or more stationary magnets, and wherein the localization signal comprises a magnetic field produced by the one or more stationary magnets.

Clause 120. The device of any one of the preceding clauses, wherein the localization unit comprises a radio frequency emitter and wherein the localization signal comprises a radio frequency signal emitted.

Clause 121. The device of any one of the preceding clauses, wherein the localization unit comprises an actuator, and wherein the localization signal comprises movement or vibration via the actuator.

Clause 122. The device of any one of the preceding clauses, wherein the localization unit comprises an actuator, and wherein the localization signal comprises protrusions rising from a surface of the device.

Clause 123. The device of any one of the preceding clauses, wherein the localization unit comprises a radioisotope, and wherein the localization signal comprises electromagnetic radiation emitted from the radioisotope Clause 124. The device of any one of the preceding clauses, wherein the localization unit comprises an ultrasound transducer, and wherein the localization signal comprises an ultrasound beam emitted from the ultrasound transducer.

Clause 125. The device of any one of the preceding clauses, wherein the localization unit comprises a heating element, and wherein the localization signal comprises an increased temperature of the heating element.

Clause 126. The device of any one of the preceding clauses, wherein the localization signal comprises patient data transmitted to the interrogation device.

Clause 127. The device of any one of the preceding clauses, further comprising one or more sensors configured to capture physiological data, and wherein the patient data comprises the captured physiological data.

Clause 128. The device of any one of the preceding clauses, wherein the sensors comprise one or more of: EKG sensors, a temperature sensor, an accelerometer, a gyroscope, a magnetometer, a pulse oximeter, a pressure sensor, a light sensor, a pH sensor, a blood-gas sensor, or a blood-chemistry sensor.

Clause 129. The device of any one of the preceding clauses, wherein the physiological data comprises one or more of: an EKG reading, a pulse rate, a blood pressure, a temperature, detected-motion data, a blood oxygenation, pH data, or blood-constituent data.

Clause 130. The device of any one of the preceding clauses, further comprising a reservoir coupled to an outlet port, and a catheter fluidically coupled to the output port.

Clause 131. The device of any one of the preceding clauses, wherein the localization unit is further configured to: detect a characteristic of the inductively coupled interrogation device; and based on the characteristic, terminate or preclude emission of the localization signal.

Clause 132. The device of any one of the preceding clauses, wherein the localization unit is further configured to: preclude emission of the localization signal if the characteristic indicates unsuitability for pairing with the interrogation device; and allow emission of the localization signal if the characteristic indicates suitability for pairing with the interrogation device.

Clause 133. The device of any one of the preceding clauses, wherein the characteristic is a field intensity threshold of the electrical energy received from the interrogation device Clause 134. The device of any one of the preceding clauses, wherein the characteristic is a frequency of the electrical energy received from the interrogation device.

Clause 135. The device of any one of the preceding clauses, wherein the characteristic is a frequency sequence of the electrical energy received from the interrogation device.

Clause 136. A method for localizing an implantable vascular access device, the method comprising: receiving, at the implantable vascular access device, an induced electrical current; in response to the induced electrical current, emitting a localization signal from the device configured to aid identification of the device position while implanted within a patient.

Clause 137. The method of any one of the preceding clauses, wherein the device does not include a battery.

Clause 138. The method of any one of the preceding clauses, further comprising emitting the localization signal only when electrical current is induced at the implantable vascular access device.

Clause 139. The method of any one of the preceding clauses, wherein the device comprises a rechargeable battery, the method further comprising receiving the induced electrical current at a conductive coil, and delivering electrical energy from the conductive coil to the rechargeable battery.

Clause 140. The method of any one of the preceding clauses, wherein emitting the localization signal comprises emitting light from a light source.

Clause 141. The method of any one of the preceding clauses, wherein emitting the localization signal comprises emitting light from a plurality of light sources disposed about the device.

Clause 142. The method of any one of the preceding clauses, wherein the emitted light is configured to transilluminate a patient's skin when the device is implanted subcutaneously.

Clause 143. The method of any one of the preceding clauses, wherein the localization signal comprises sound emitted from a speaker.

Clause 144. The method of any one of the preceding clauses, wherein the localization signal comprises a magnetic field induced by a conductive coil.

Clause 145. The method of any one of the preceding clauses, wherein the localization signal comprises a magnetic field produced by one or more stationary magnets.

Clause 146. The method of any one of the preceding clauses, wherein the localization signal comprises a radio frequency signal.

Clause 147. The method of any one of the preceding clauses, wherein the localization signal comprises movement or vibration via an actuator.

Clause 148. The method of any one of the preceding clauses, wherein the localization signal comprises protrusions raised from a surface of the device via one or more actuators.

Clause 149. The method of any one of the preceding clauses, wherein the localization signal comprises electromagnetic radiation emitted from a radioisotope Clause 150. The method of any one of the preceding clauses, wherein the localization signal comprises an ultrasound beam emitted from an ultrasound transducer.

Clause 151. The method of any one of the preceding clauses, wherein the localization signal comprises an increased temperature of a heating element.

Clause 152. The method of any one of the preceding clauses, wherein the localization signal comprises patient data transmitted to the interrogation device.

Clause 153. The method of any one of the preceding clauses, wherein the device further comprises one or more sensors configured to capture physiological data, and wherein the patient data comprises the captured physiological data.

Clause 154. The method of any one of the preceding clauses, wherein the sensors comprise one or more of: EKG sensors, a temperature sensor, an accelerometer, a gyroscope, a magnetometer, a pulse oximeter, a pressure sensor, a light sensor, a pH sensor, a blood-gas sensor, or a blood-chemistry sensor.

Clause 155. The method of any one of the preceding clauses, wherein the physiological data comprises one or more of: an EKG reading, a pulse rate, a blood pressure, a temperature, detected-motion data, a blood oxygenation, pH data, or blood-constituent data.

Clause 156. The method of any one of the preceding clauses, further comprising: detecting a characteristic of the inductively coupled interrogation device; and based on the characteristic, terminating or precluding emission of the localization signal.

Clause 157. The method of any one of the preceding clauses, further comprising: precluding emission of the localization signal if the characteristic indicates unsuitability for pairing with the interrogation device; and allowing emission of the localization signal if the characteristic indicates suitability for pairing with the interrogation device.

Clause 158. The method of any one of the preceding clauses, wherein the characteristic is a field intensity threshold of the electrical energy received from the interrogation device Clause 159. The method of any one of the preceding clauses, wherein the characteristic is a frequency of the electrical energy received from the interrogation device.

Clause 160. The method of any one of the preceding clauses, wherein the characteristic is a frequency sequence of the electrical energy received from the interrogation device.

Clause 170. A method for localizing an implantable vascular access device, the method comprising: providing a vascular access device configured to emit a localization signal in response to an induced electrical current; placing an interrogation device into proximity with the vascular access device, the interrogation device including a conductive coil; and applying current to the conductive coil, thereby inducing electrical current at the vascular access device, and causing the vascular access device to emit the localization signal.

Clause 171. The method of any one of the preceding clauses, further comprising aligning the interrogation device with the vascular access device based at least in part on the localization signal.

Clause 172. The method of any one of the preceding clauses, wherein the interrogation device further comprises a body defining an aperture, the conductive coil being disposed within the body, and wherein aligning the interrogation device with the vascular access device comprises aligning the aperture with the vascular access device.

Clause 173. The method of any one of the preceding clauses, wherein aligning the aperture with the vascular access device comprises aligning the aperture with a self-sealing cover of a reservoir of the vascular access device.

Clause 174. The method of any one of the preceding clauses, further comprising passing a needle through the aperture of the interrogation device, through the self-sealing cover of the reservoir, and into the reservoir of the vascular access device.

Clause 175. The method of any one of the preceding clauses, further comprising delivering fluid through the needle and into the reservoir of the vascular access device.

Clause 176. The method of any one of the preceding clauses, wherein the aperture comprises a membrane.

Clause 177. The method of any one of the preceding clauses, wherein the membrane comprises an adhesive.

Clause 178. The method of any one of the preceding clauses, wherein placing the interrogation device into proximity with the vascular access device comprises contacting the interrogation device to a patient's skin proximate to the implanted vascular access device.

Clause 179. The method of any one of the preceding clauses, wherein the interrogation device comprises an adhesive, and wherein contacting the interrogation device to the patient's skin comprises adhering the interrogation device to the patient's skin.

Clause 180. The method of any one of the preceding clauses, wherein the adhesive is antimicrobial.

Clause 181. An implantable vascular access device comprising: a fluid reservoir; a self-sealing cover disposed over the reservoir; an outlet port configured to mate with a catheter, the outlet port fluidically coupled to the fluid reservoir; one or more sensors configured to capture physiological data while the device is implanted within a patient; a data communications unit configured to receive physiological data from the one or more sensors and transmit the physiological data to one or more remote computing devices; a battery electrically coupled to the data communications unit; and a wireless charging unit electrically coupled to the battery, the wireless charging unit configured to recharge the battery in the presence of a wireless power transmission.

Clause 182. The device of any one of the preceding clauses, wherein the wireless charging unit comprises a conductive coil configured to deliver electrical energy to the battery in response an alternating magnetic field.

Clause 183. The device of any one of the preceding clauses, wherein the sensors comprise one or more of: EKG sensors, a temperature sensor, an accelerometer, a gyroscope, a magnetometer, a pulse oximeter, a pressure sensor, a light sensor, a pH sensor, a blood-gas sensor, or a blood-chemistry sensor.

Clause 184. The device of any one of the preceding clauses, wherein the physiological data comprises one or more of: an EKG reading, a pulse rate, a blood pressure, a temperature, detected-motion data, a blood oxygenation, pH data, or blood-constituent data.

Clause 185. The device of any one of the preceding clauses, further comprising a catheter fluidically coupled to the output port.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

Figure 1:
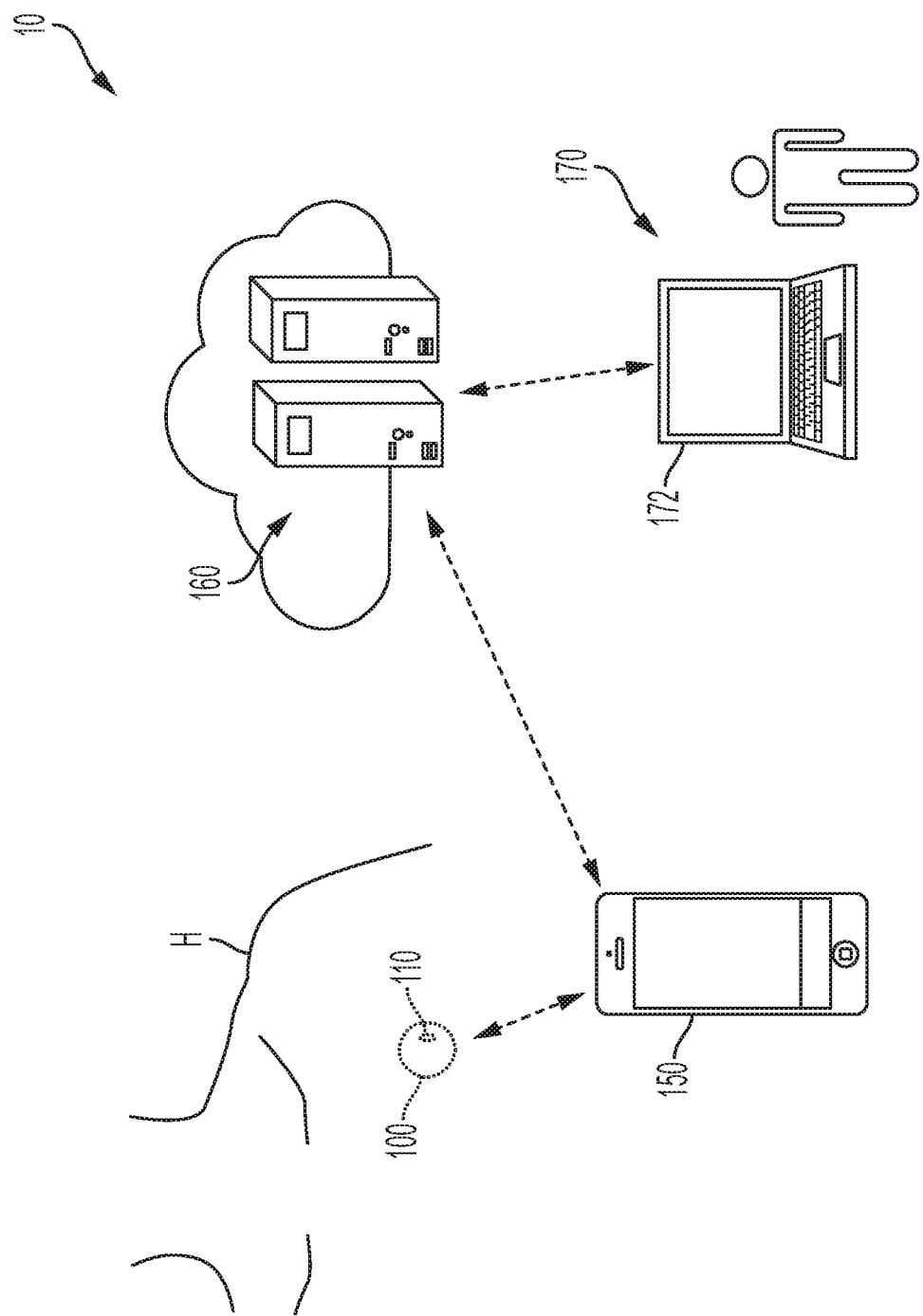
FIG. 1 is a schematic representation of a system for monitoring the health of a patient via an implanted medical device in accordance with the present technology.

The present technology relates to implantable medical devices such as vascular access devices and associated systems and methods of use. Some embodiments of the present technology, for example, are directed to wireless charging and localization of such implantable devices. Some embodiments are directed to methods and systems for secure data communication between an implantable device and external computing devices. Specific details of several embodiments of the technology are described below with reference to FIGS. 1-9B.

Conventional vascular access devices are bulky by design to allow a clinician to localize the device by palpation. To be accurately accessed by a clinician, the vascular access device needs to be either visualized or palpated under the skin. Reducing the profile and/or the footprint of the device may improve patient comfort. However, this reduction may render the device more difficult to locate using palpation alone. Additionally, conventional vascular access ports have no electronic components and do not require an internal power source.

Advanced vascular access devices may be equipped with electronic components to provide a platform for remote patient monitoring technology. For example, an implanted vascular access device may contain an array of physiologic sensors that monitor a patient's physiological parameters, enabling early warning systems, alerting patients and their healthcare teams when there is a risk of illness or complications from therapy. Additionally, the implanted device may contain data storage and communication technology that not only monitors physiologic parameters, but also contains information about the patient's demographics, diagnoses, treatment history, and POLST (Physician Order for Life Sustaining Treatment) status.

As described in more detail below, a vascular access device equipped with physiological sensors and other electronics may be configured for wireless communication with an interrogation device or other remote computing device. In response to communication with the interrogation device, the vascular access device may emit a localization signal that facilitates a clinician's identification of the location of the device. For example, the localization signal can be emitted light that transilluminates a patient's skin, vibrating elements, magnets that create a signature magnetic field, etc. The interrogation device may also wirelessly recharge a battery of the vascular access device, for example via inductive charging.

In some embodiments, the vascular access device may transmit patient data (e.g., physiological measurements, patient medical record data, etc.) to the interrogation device or other remote computing device. Storage and transmission of such sensitive patient data require new techniques for maintaining data security while enabling remote monitoring and communication. Currently available electronically controlled implantable devices exist, including pacemakers, defibrillators, and nerve stimulators. Some of these devices wirelessly communicate data to physicians through home base stations or by telephone, inciting patient data security concerns. Conventional wearable monitors also illicit privacy concerns related to traceability of location, as well as personal physiological data. In some cases, these data have generated security concerns for military personnel. Next generation data security innovations are necessary to combat these privacy and security concerns. Accordingly, as described in more detail below, the vascular access device may obfuscate the patient data (e.g., using a combination of encryption and other related techniques) to maintain security of the data while transmitting the data wirelessly to the interrogation device.

Patient Monitoring System Overview

FIG. 1 is a schematic representation of a system 10 for monitoring the health of a patient via a vascular access device 100 (or "device 100") in accordance with the present technology. The device 100 is configured to be implanted within a human patient H, such as at a subcutaneous location along an upper region of the patient's chest. As shown in FIG. 1, the device 100 may include a sensing element 110 configured to obtain physiological measurements that are used by the system 10 to determine one or more physiological parameters indicative of the patient's health. In some embodiments, the system 10 may detect a medical condition (such as sepsis) or associated symptom(s) based on the physiological parameter(s) and provide an indication of the detected condition to the patient, caregiver, and/or medical care team.

As shown schematically in FIG. 1, the device 100 may be configured to communicate wirelessly with a local computing device 150, which can be, for example, a smart device (e.g., a smartphone, a tablet, or other handheld device having a processor and memory), a special-purpose interrogation device, or other suitable device. Communication between the device 100 and the local computing device 150 can be mediated by, for example, near-field communication (NFC), infrared wireless, Bluetooth, ZigBee, Wi-Fi, inductive coupling, capacitive coupling, or any other suitable wireless communication link. The device 100 may transmit data including, for example, physiological measurements obtained via the sensing element 110, patient medical records, device performance metrics (e.g., battery level, error logs, etc.), or any other such data stored by the device 100. In some embodiments, the transmitted data is encrypted or otherwise obfuscated to maintain security during transmission to the local computing device 150. The local computing device 150 may also provide instructions to the vascular access device 100, for example to obtain certain physiological measurements via the sensing element 110, to emit a localization signal, or to perform other functions. In some embodiments, the local computing device 150 may be configured to wirelessly recharge a battery of the device 100, for example via inductive charging.

The system 10 may further include first remote computing device(s) 160 (or server(s)), and the local computing device 150 may in turn be in communication with first remote computing device(s) 160 over a wired or wireless communications link (e.g., the Internet, public and private intranet, a local or extended Wi-Fi network, cell towers, the plain old telephone system (POTS), etc.). The first remote computing device(s) 160 may include one or more own processor(s) and memory. The memory may be a tangible, non-transitory computer-readable medium configured to store instructions executable by the processor(s). The memory may also be configured to function as a remote database, i.e., the memory may be configured to permanently or temporarily store data received from the local computing device 150 (such as one or more physiological measurements or parameters and/or other patient information).

In some embodiments, the first remote computing device(s) 160 can additionally or alternatively include, for example, server computers associated with a hospital, a medical provider, medical records database, insurance company, or other entity charged with securely storing patient data and/or device data. At a remote location 170 (e.g., a hospital, clinic, insurance office, medical records database, operator's home, etc.), an operator may access the data via a second remote computing device 172, which can be, for example a personal computer, smart device (e.g., a smartphone, a tablet, or other handheld device having a processor and memory), or other suitable device. The operator may access the data, for example, via a web-based application. In some embodiments, the obfuscated data provided by the device 100 can be de-obfuscated (e.g., unencrypted) at the remote location 170.

In some embodiments, the device 100 may communicate with remote computing devices 160 and/or 170 without the intermediation of the local computing device 150. For example, the vascular access device 100 may be connected via Wi-Fi or other wireless communications link to a network such as the Internet. In other embodiments, the device 100 may be in communication only with the local computing device 150, which in turn is in communication with remote computing devices 160 and/or 170.

Figure 2:
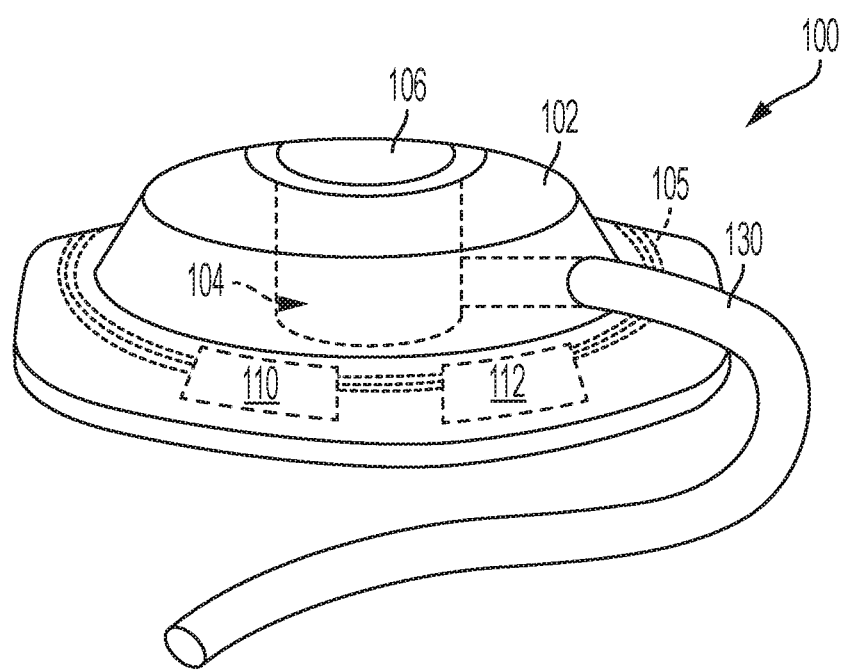
FIG. 2 shows an example of a vascular access device configured for use with the system of FIG. 1.

FIG. 2 shows an example of a vascular access device 100 (or "device 100") configured for use with the system 10 of the present technology. As shown in FIG. 2, the device 100 comprises a housing 102 configured to be implanted within a human patient, a fluid reservoir 104 contained within the housing 102, and a self-sealing septum 106 adjacent the reservoir 104 and configured to receive a needle therethrough for delivery of a therapeutic agent to the reservoir 104 (as described in greater detail below with respect to FIG. 3). The housing 102 may be made of a biocompatible plastic, metal, ceramic, medical grade silicone, or other material that provides sufficient rigidity and strength to prevent needle puncture. The self-sealing septum 106 can be, for example, a membrane made of silicone or other deformable, self-sealing, biocompatible material. In some embodiments, the device 100 may include a catheter 130 that extends distally from the housing 102 and is in fluid communication with the reservoir 104. For example, the catheter 130 can be configured to mate with an outlet port of the device 100 via a barb connector or other suitable mechanical connection. The catheter 130 may be a single or multi-lumen catheter. In some embodiments, the device 100 includes multiple separate catheters.

Figure 3:
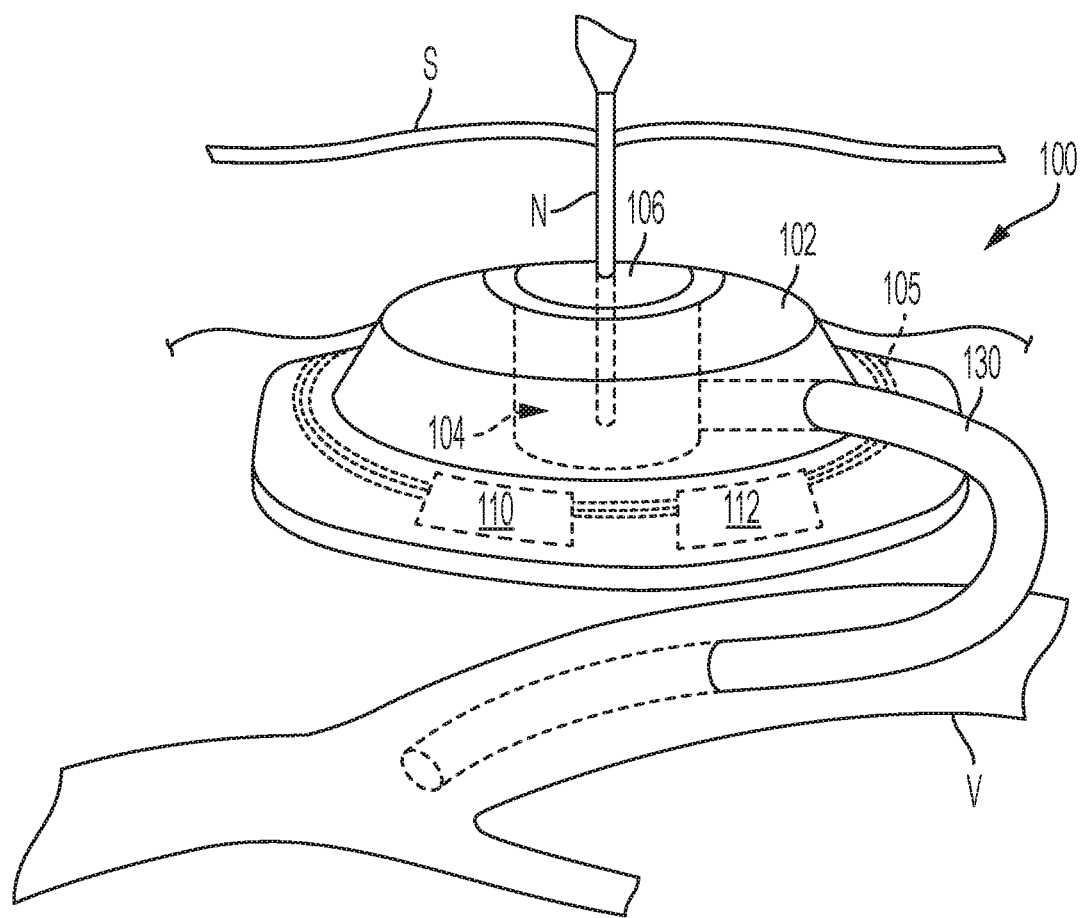
FIG. 3 shows the vascular access device of FIG. 2 implanted within a patient's body.

As shown in FIG. 3, in operation the device 100 is implanted in a patient beneath the skin S, for example in a small pocket created in the upper chest wall just inferior to the clavicle. The catheter 130, which is in fluid communication with the reservoir 104, is inserted into a blood vessel V, for example the internal jugular vein or the subclavian vein with the tip resting in the superior vena cava or the right atrium. A clinician inserts a needle N (e.g., a non-coring or Huber-type needle) through the skin S, through the self-sealing septum 106, and into the fluid reservoir 104. To introduce fluid (e.g., medication) into the patient's blood vessel V, the clinician may advance fluid through the needle N, which then flows through the reservoir 104, the catheter 130, and into the vessel V, or the physician may advance fluid through the needle to fill the reservoir for postponed delivery into the vessel V. To remove fluid from the vessel V (e.g., to aspirate blood from the vessel V for testing), the clinician can apply suction via the needle N, thereby withdrawing fluid (e.g., blood) from the vessel V into the catheter 130, into the fluid reservoir 104, and into the needle N. When the procedure is completed, the clinician removes the needle N, the self-sealing septum 106 resumes a closed configuration, and the device 100 may remain in place beneath the patient's skin S.

Referring again to FIG. 2, as previously mentioned, the device 10 includes a sensing element 110 coupled to the housing 102 and configured to obtain physiological measurements. Although a single sensing element 110 is illustrated for clarity, in various embodiments, the device 100 may include a plurality of sensing elements 110 disposed within or otherwise coupled to the housing 102. In some embodiments, one or more such sensing elements 110 may be disposed on separate structural components that are separated from the housing 102. As used herein, the term "sensing element" may refer to a single sensor or a plurality of discrete, separate sensors.

The device 100 may include at least one controller 112 communicatively coupled to the sensing element 110. The controller 112 may include one or more processors, software components, and memory (not shown). In some examples, the one or more processors include one or more computing components configured to process the physiological measurements received from the sensing element 110 according to instructions stored in the memory. The memory may be a tangible, non-transitory computer-readable medium configured to store instructions executable by the one or more processors. For instance, the memory may be data storage that can be loaded with one or more of the software components executable by the one or more processors to achieve certain functions. In some examples, the functions may involve causing the sensing element 110 to obtain physiological data from the patient. In another example, the functions may involve processing the physiological data to determine one or more physiological parameters and/or provide an indication to the patient and/or clinician of one or more symptoms or medical conditions associated with the determined physiological parameters.

The controller 112 may also include a data communications unit configured to securely transmit data between the device 100 and external computing devices (e.g., local computing device 150, remote computing devices 160 and 170, etc.). In some embodiments, the controller 112 includes a localization unit configured to emit a localization signal (e.g., lights that transilluminate a patient's skin, vibration, a magnetic field, etc.) to aid a clinician in localizing the device 100 when implanted within a patient. The controller 112 can also include a wireless charging unit 105 (such as a coil) configured to recharge a battery (not shown) of the device 100 when in the presence of an interrogation device (e.g., local device 150 or another suitable device).

The system 10 may be configured to continuously and/or periodically obtain physiological measurements via the sensing element 110 in communication with the device 100. The sensing element 110 may be carried by the housing 102 and/or the catheter 130, and/or may include a sensing component separate from the housing 102 and catheter 130 but physically or communicatively coupled to the housing 102 and/or catheter 130. The sensing element 110 may be implanted at the same location as the device 100 or at a different location, or may be positioned on the patient at an exterior location (e.g., on the patient's skin). The sensing element 110 may be permanently coupled to the device 100, or may be configured to temporarily couple to the device 100.

In some embodiments, the sensing element 110 is built into the housing 102 such that only a portion of the sensing element 110 is exposed to the local physiological environment when the device 100 is implanted. For example, the sensing element 110 may comprise one or more electrodes having an external portion positioned at an exterior surface of the housing 102 and an internal portion positioned within the housing 102 and wired to the controller 112. In some embodiments the sensing element 110 may be completely contained within the housing 102. For example, the sensing element 110 may comprise a pulse oximeter enclosed by the housing 102 and positioned adjacent a window in the housing 102 through which light emitted from the pulse oximeter may pass to an external location, and back through which light reflected from the external location may pass for detection by a photodiode of the pulse oximeter. In such embodiments the window may be, for example, a sapphire window that is brazed into place within an exterior wall of the housing 102.

The sensing element 110 may comprise at least one sensor completely enclosed by the housing 102 and at least one sensor that is partially or completely positioned at an external location, whether directly on the housing 102 and/or catheter 130 or separated from the housing 102 and/or catheter 130 (but still physically coupled to the housing 102 and/or catheter 130 via a wired connection, for example.)

In some embodiments, the sensing element 110 may include a separate controller (not shown) that comprises one or more processors and/or software components. In such embodiments, the sensing element 110 may process at least some of the physiological measurements to determine one or more physiological parameters, and then transmit those physiological parameters to the controller 112 of the device 100 (with or without the underlying physiological data). In some examples, the sensing element 110 may only partially process at least some of the physiological measurements before transmitting the data to the controller 112. In such embodiments, the controller 112 may further process the received physiological data to determine one or more physiological parameters. The local computing device 150 and/or the remote computing devices 160, 170 may also process some or all of the physiological measurements obtained by the sensing element 110 and/or physiological parameters determined by the sensing element 110 and/or the controller 112.

According to some aspects of the technology, the sensing element 110 may include memory. The memory may be a non-transitory computer-readable medium configured to permanently and/or temporarily store the physiological measurements obtained by the sensing element 110. In those embodiments where the sensing element 110 includes its own processor(s), the memory may be a tangible, non-transitory computer-readable medium configured to store instructions executable by the processor(s).

In some embodiments, the sensing element(s) 110 and/or controller 112 may identify, monitor, and communicate patient information by electromagnetic, acoustic, motion, optical, thermal, or biochemical sensing elements or means. The sensing element(s) 110 may include, for example, one or more temperature sensing elements (e.g., one or more thermocouples, one or more thermistors or other type of resistance temperature detector, etc.), one or more impedance sensing elements (e.g., one or more electrodes), one or more pressure sensing elements, one or more optical sensing elements, one or more flow sensing elements (e.g., a Doppler velocity sensing element, an ultrasonic flow meter, etc.), one or more ultrasonic sensing elements, one or more pulse oximeters, one or more chemical sensing elements, one or more movement sensing elements (e.g., one or more accelerometers), one or more pH sensing elements, an electrocardiogram ("ECG") unit, one or more electrochemical sensing elements, one or more hemodynamic sensing elements, and/or other suitable sensing devices.

The sensing element 110 may comprise one or more electromagnetic sensing elements configured to measure and/or detect, for example, impedance, voltage, current, or magnetic field sensing capability with a wire, wires, wire bundle, magnetic node, and/or array of nodes. The sensing element 110 may comprise one or more acoustic sensing elements configured to measure and/or detect, for example, sound frequency, within human auditory range or below or above frequencies of human auditory range, beat or pulse pattern, tonal pitch melody, and/or song. The sensing element 110 may comprise one or more motion sensing elements configured to measure and/or detect, for example, vibration, movement pulse, pattern or rhythm of movement, intensity of movement, and/or speed of movement. Motion communication may occur by a recognizable response to a signal. This response may be by vibration, pulse, movement pattern, direction, acceleration, or rate of movement. Motion communication may also be by lack of response, in which case a physical signal, vibration, or bump to the environment yields a motion response in the surrounding tissue that can be distinguished from the motion response of the sensing element 110. Motion communication may also be by characteristic input signal and responding resonance. The sensing element 110 may comprise one or more optical sensing elements which may include, for example, illuminating light wavelength, light intensity, on/off light pulse frequency, on/off light pulse pattern, passive glow or active glow when illuminated with special light such as UV or "black light", or display of recognizable shapes or characters. It also includes characterization by spectroscopy, interferometry, response to infrared illumination, and/or optical coherence tomography. The sensing element 110 may comprise one or more thermal sensing elements configured to measure and/or detect, for example, device 100 temperature relative to surrounding environment, the temperature of the device 100 (or portion thereof), the temperature of the environment surrounding the device 100 and/or sensing element 110, or differential rate of the device temperature change relative to surroundings when the device environment is heated or cooled by external means. The sensing element 110 may comprise one or more biochemical devices which may include, for example, the use of a catheter, a tubule, wicking paper, or wicking fiber to enable micro-fluidic transport of bodily fluid for sensing of protein, RNA, DNA, antigen, and/or virus with a micro-array chip.

In some aspects of the technology, the controller 112 and/or sensing element 110 may be configured to detect and/or measure the concentration of blood constituents, such as sodium, potassium, chloride, bicarbonate, creatinine, blood urea nitrogen, calcium, magnesium, and phosphorus. The system 10 and/or the sensing element 110 may be configured to evaluate liver function (e.g., by evaluation and/or detection of AST, ALT, alkaline phosphatase, gamma glutamyl transferase, troponin, etc.), heart function (e.g., by evaluation and/or detection of troponin), coagulation (e.g., via determination of prothrombin time (PT), partial thromboplastin time (PTT), and international normalized ratio (INR)), and/or blood counts (e.g., hemoglobin or hematocrit, white blood cell levels with differential, and platelets). In some embodiments, the system 10 and/or the sensing element 110 may be configured to detect and/or measure circulating tumor cells, circulating tumor DNA, circulating RNA, multigene sequencing of germ line or tumor DNA, markers of inflammation such as cytokines, C reactive protein, erythrocyte sedimentation rate, tumor markers (PSA, beta-HCG, AFP, LDH, CA 125, CA 19-9, CEA, etc.), and others.

As previously mentioned, the system 10 may determine one or more physiological parameters based on the physiological measurements and/or one or more other physiological parameter(s). For example, the system 10 may be configured to determine physiological parameters such as heart rate, temperature, blood pressure (e.g., systolic blood pressure, diastolic blood pressure, mean blood pressure), blood flow rate, blood velocity, pulse wave speed, volumetric flow rate, reflected pressure wave amplitude, augmentation index, flow reserve, resistance reserve, resistive index, capacitance reserve, hematocrit, heart rhythm, electrocardiogram (ECG) tracings, body fat percentage, activity level, body movement, falls, gait analysis, seizure activity, blood glucose levels, drug/medication levels, blood gas constituents and blood gas levels (e.g., oxygen, carbon dioxide, etc.), lactate levels, hormone levels (such as cortisol, thyroid hormone (T4, T3, free T4, free T3), TSH, ACTH, parathyroid hormone), and/or any correlates and/or derivatives of the foregoing measurements and parameters (e.g., raw data values, including voltages and/or other directly measured values). In some embodiments, one or more of the physiological measurements can be utilized or characterized as a physiological parameter without any additional processing by the system 10.

The system 10 may also determine and/or monitor derivatives of any of the foregoing physiological parameters (also referred to herein as "physiological parameters"), such as a rate of change of a particular parameter, a change in a particular parameter over a particular time frame, etc. As but a few examples, the system 10 may be configured to determine as temperature over a specified time, a maximum temperature, a maximum average temperature, a minimum temperature, a temperature at a predetermined or calculated time relative to a predetermined or calculated temperature, an average temperature over a specified time, a maximum blood flow, a minimum blood flow, a blood flow at a predetermined or calculated time relative to a predetermined or calculated blood flow, an average blood flow over time, a maximum impedance, a minimum impedance, an impedance at a predetermined or calculated time relative to a predetermined or calculated impedance, a change in impedance over a specified time, a change in impedance relative to a change in temperature over a specified time, a change in heart rate over time, a change in respiratory rate over time, activity level over a specified time and/or at a specified time of day, and other suitable derivatives.

Measurements may be obtained continuously or periodically at one or more predetermined times, ranges of times, calculated times, and/or times when or relative to when a measured event occurs. Likewise, physiological parameters may be determined continuously or periodically at one or more predetermined times, ranges of times, calculated times, and/or times when or relative to when a measured event occurs.

Based on the determined physiological parameters, the system 10 of the present technology is configured to provide an indication of the patient's health to the patient and/or a clinician. For example, the controller 112 may compare one or more of the physiological parameters to a predetermined threshold or range and, based on the comparison, provide an indication of the patient's health. For instance, if the determined physiological parameter(s) is above or below the predetermined threshold or outside of the predetermined range, the system 10 may provide an indication that the patient is at risk of, or has already developed, a medical condition characterized by symptoms associated with the determined physiological parameters. As used herein, a "predetermined range" refers to a set range of values, and "outside of a/the predetermined range" refers to (a) a measured or calculated range of values that only partially overlap the predetermined range or do not overlap any portion of a predetermined range of values. As used herein, a "predetermined threshold" refers to a single value or range of values, and a parameter that is "outside" of "a predetermined threshold" refers to a situation where the parameter is (a) a measured or calculated value that exceeds or fails to meet a predetermined value, (b) a measured or calculated value that falls outside of a predetermined range of values, (c) a measured or calculated range of values that only partially overlaps a predetermined range of values or does not overlap any portion of a predetermined range of values, or (d) a measured or calculated range of values where none of the values overlap with a predetermined value.

Predetermined parameter thresholds and/or ranges can be empirically determined to create a look-up table. Look-up table values can be empirically determined, for example, based on clinical studies and/or known healthy or normal values or ranges of values. The predetermined threshold may additionally or alternatively based on a particular patient's baseline physiological parameters.

Medical conditions detected and/or indicated by the system 10 may include, for example, sepsis, pulmonary embolism, metastatic spinal cord compression, anemia, dehydration/volume depletion, vomiting, pneumonia, congestive heart failure, performance status, arrythmia, neutropenic fever, acute myocardial infarction, pain, opioid toxicity, nicotine or other drug addiction or dependency, hyperglycemic/diabetic ketoacidosis, hypoglycemia, hyperkalemia, hypercalcemia, hyponatremia, one or more brain metastases, superior vena cava syndrome, gastrointestinal hemorrhage, immunotherapy-induced or radiation pneumonitis, immunotherapy-induced colitis, diarrhea, cerebrovascular accident, stroke, pathological fracture, hemoptysis, hematemesis, medication-induced QT prolongation, heart block, tumor lysis syndrome, sickle cell anemia crisis, gastroparesis/cyclic vomiting syndrome, hemophilia, cystic fibrosis, chronic pain, and/or seizure.

Figure 4:
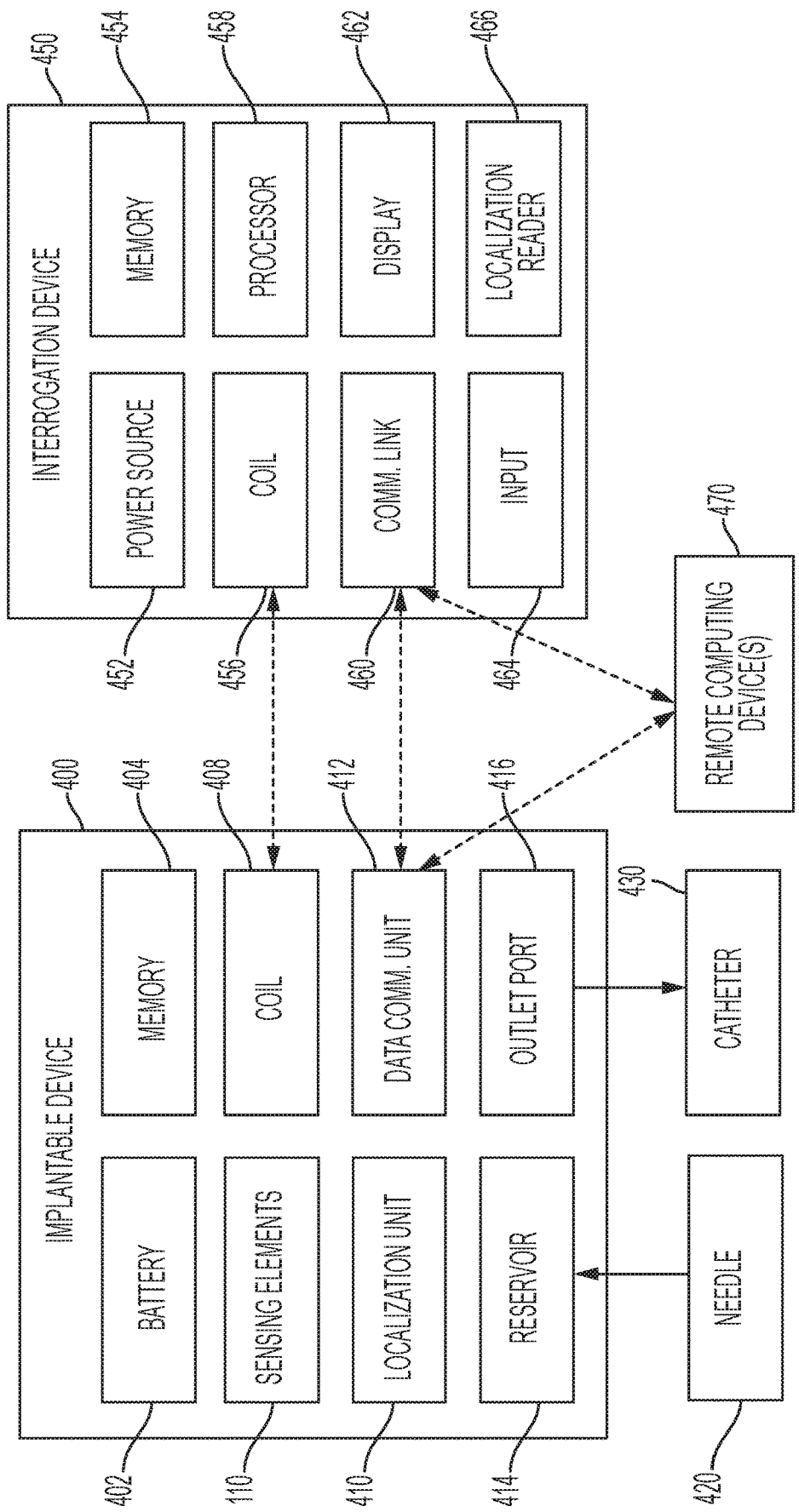
FIG. 4 is a schematic block diagram of an environment for communication between an implantable device, an interrogation device, and one or more remote computing devices in accordance with the present technology.

FIG. 4 is a schematic block diagram of an environment for communication between an implantable device 400, an interrogation device 450, and one or more remote computing devices 470. The implantable device 400 can be a vascular access device (e.g., the device 100 described above with respect to FIGS. 1-3). In some embodiments, the implantable device 400 can be another implantable medical device, for example, a pacemaker, implantable cardioverter/defibrillator (ICD), deep brain stimulator, insulin pump, infusion port, orthopedic device, pulmonary artery pressure monitor, or any other implantable medical device with electronic sensing components.

The interrogation device 450 can be, for example, a handheld device configured to communicate wirelessly with the implantable device 400 when the device 400 is implanted within a patient. This communication can be carried out using a short-range connection (e.g., near-field communication (NFC), infrared wireless, Bluetooth, ZigBee, Wi-Fi, inductive coupling, or capacitive coupling) or other suitable wireless communication link. In various embodiments, the implantable device 400 and/or the interrogation device 450 can communicate with one or more remote computing devices 470, for example over a network connection such as the Internet.

In the illustrated embodiment, the implantable device 400 can include a battery 402 (e.g., a rechargeable battery or other power source), and memory 404. The memory 404 can include read-only memory (ROM) and random access memory (RAM) or other storage devices such as SSDs that store the executable applications, test software, databases and other software required to, for example, implement the various routines described herein, control device components, communicate and exchange data and information with remote computers and other devices, etc. The implantable device 400 can include a number of electronic elements (e.g., the memory 404, sensing elements 110, coil 408, the localization unit 410, and/or the data communications unit 412). Some or all of these elements can include one or more processors, analog-to-digital converters, data storage devices, wireless communication antennas, and other associated elements. Some or all of these elements can be electronically coupled to or carried by a printed circuit board (e.g., a rigid or flexible PCB) or other suitable substrate. In some embodiments, software or firmware stored in the memory 404 or on a microprocessor unit can be configured to optimize data collection, communication, localization, and battery life of the device 400.

The implantable device 400 includes sensing elements 110 configured to obtain one or more physiological measurements while implanted within the body. As described above with respect to FIGS. 1-3, the sensor elements 110 can be configured to obtain any number of different physiological measurements and/or one or more other physiological parameters. For the example, the sensor elements 110 may be configured to determine physiological parameters such as heart rate, temperature, blood pressure (e.g., systolic blood pressure, diastolic blood pressure, mean blood pressure), blood flow rate, blood velocity, pulse wave speed, volumetric flow rate, reflected pressure wave amplitude, augmentation index, flow reserve, resistance reserve, resistive index, capacitance reserve, hematocrit, heart rhythm, electrocardiogram (ECG) tracings, body fat percentage, activity level, body movement, falls, gait analysis, seizure activity, blood glucose levels, drug/medication levels, blood gas constituents and blood gas levels (e.g., oxygen, carbon dioxide, etc.), lactate levels, hormone levels (such as cortisol, thyroid hormone (T4, T3, free T4, free T3), TSH, ACTH, parathyroid hormone), and/or any correlates and/or derivatives of the foregoing measurements and parameters (e.g., raw data values, including voltages and/or other directly measured values).

The device 400 can also include a coil 408, for example a length of electrically conductive wire or other material that is wrapped to form a circular coil or other shape. In some embodiments, the coil 408 can be a conductive wire that encircles the reservoir 414 of the device 400. The coil 408 can be electrically coupled to the battery 402 such that electrical energy received via the coil 408 can be used to recharge the battery 402. The coil 408 can also be electrically coupled to the localization unit 410 such that electrical energy received via the coil 408 causes the localization unit 410 to emit a localization signal. Additionally, the coil 408 can be electrically coupled to the data communications unit 412 such that electrical energy received via the coil 408 causes the data communications unit 412 to perform certain actions, for example securely transmitting data to the interrogation device 450. As described in more detail below, the coil 408 can be inductively coupled to a coil 456 of the interrogation device 450 to wirelessly receive electrical energy from the coil 456. In some embodiments, the wireless energy is transmitted via capacitive coupling rather than inductive coupling.

With continued reference to FIG. 4, the implantable device 400 further includes a localization unit 410. The localization unit 410 can include an emitter configured to emit a localization signal in addition to a controller (e.g., a central processing unit, digital signal processor, application-specific integrated circuit, or any other logic processing unit) that reads instructions from the memory 404 to perform suitable operations or performs operations based on firmware stored on a microprocessor unit. The localization unit 410 can be configured to emit one or more localization signals from the implantable device 400 to aid a clinician in identifying the location of the device 400 when implanted within a patient. As noted previously, in some embodiments the localization unit 410 is configured to emit a localization signal in response to detecting the presence of the interrogation device 450. For example, the coil 456 of the interrogation device 450 can be driven with an alternating current suitable to induce a current in the coil 408 of the implantable device 400 when the two devices are held in proximity to one another. The induced electrical current in the coil 408 of the implantable device can, in turn, cause the localization unit 410 to emit a localization signal. In some embodiments, the interrogation device 450 can include a localization reader 466 that is configured to read, detect, or otherwise identify a localization signal emitted by the localization unit 410 of the implantable device 410. In other embodiments, the localization reader 466 can be omitted from the interrogation device 450, and a clinician may directly observe the localization signal emitted by the localization unit 450.

In various embodiments, the localization unit 410 can take a variety of forms, having different configurations of emitters configured to emit different localization signals, and a corresponding localization reader 466 of the interrogation device 450 can be configured to read or detect the particular localization signal emitted by the localization unit 410. In each of the following examples, in some embodiments the interrogation device 450 may not include a localization reader 466, and instead the localization signal emitted from the localization unit 410 of the implantable device 400 may be read, observed, or detected either directly by the clinician or by using another suitable instrument. In one example, the localization unit 410 can include one or more light sources disposed about the device 100, and the localization signal can include the emission of light from the light sources. The emitted light can be configured to transilluminate the skin to indicate a location of the implantable device 400 to a clinician. In this instance, the localization reader 466 can include a light sensor or array of sensors configured to identify the lights transilluminating the patient's skin.

In further examples, the localization signal may take a variety of other forms. In some embodiments, the localization unit 410 includes a speaker configured to emit an audible sound as the localization signal, and the localization reader 466 includes a microphone or other device configured to detect the emitted sound and to localize its source. In some embodiments, the localization unit 410 includes one or more magnets (e.g., permanent magnets or electromagnets), and the localization signal includes the magnetic field generated by the magnets. For example, a plurality of magnets may be disposed around a reservoir of the implantable device 400, and the magnetic field generated by these magnets may be detected by the localization reader 466 of the interrogation device 450 in a manner that indicates the location of the reservoir or other aspect of the implantable device 400. In some embodiments, the localization unit 410 includes a radiofrequency transmitter, and the localization signal includes a radiofrequency signal that can be detected by the interrogation device 450. In this instance, the localization reader 466 can be an antenna or other device configured to detect the signature radiofrequency signal emitted by the interrogation device and to localize the source of the signals. In some embodiments, the localization unit 410 includes an actuator configured to move or vibrate certain elements to serve as the localization signal. In some embodiments, the localization unit 410 includes one or more ultrasound transducers, and the emitted ultrasound serves as a localization signal to be detected by the localization reader 466 interrogation device 450. In some embodiments, the localization unit 410 includes at least one moveable member that can create temporary a protrusion raising from an upper surface of the implantable device such that the protrusion can be palpated by a clinician to localize the device 400. In some embodiments, the localization unit 410 includes a radioisotope and the localization signal comprises the electromagnetic radiation emitted by the radioisotope. For example, the localization unit 410 may include a retractable shield that absorbs radiation emitted by the radioisotope. To emit the localization signal, the localization unit 410 can cause the shield to be retracted, thereby allowing the radiation emitted by the radioisotope to escape the device 400 to be detected by the localization reader 466 of the interrogation device 450. In some embodiments, the localization unit 410 includes a heating element and the localization signal is the increased heat signature radiating from the heating element. The increased temperature can be detected via a thermal camera, temperature sensor, or other suitable element of the localization reader 466. In some embodiments, the localization unit 410 can cause the data communications unit 412 to send patient data or other identifying data to serve as a localization signal. The localization reader 466 may identify the source of the signal by triangulating its position to identify the location of the device 400.

In some embodiments, the localization unit 410 determines whether to emit a localization signal based on a characteristic of the interrogation device 450 that induces a current in the coil 408 of the implantable device 400. For example, the localization unit 410 may assess a characteristic such as a field intensity threshold of electrical energy received from the interrogation device 450, a frequency of the electrical energy received from the interrogation device 450, etc. These characteristics can aid in discriminating between a trusted interrogation device (i.e. an interrogation device suitable for pairing) and a non-trusted interrogation device (i.e., an interrogation device unsuitable for pairing), such that only pre-authorized interrogation devices 450 are able to cause the localization unit 410 to emit a localization signal.

The implantable device 400 also includes a data communications unit 412 that is configured to communicate wirelessly with the interrogation device 450 (via communications link 460). Communication between the data communications unit 412 and the interrogation device 450 can be mediated by, for example, near-field communication (NFC), infrared wireless, Bluetooth, ZigBee, Wi-Fi, inductive coupling, capacitive coupling, or any other suitable wireless communication link. The data communications unit 412 may transmit data including, for example, physiological measurements obtained via the sensing elements 110, patient medical records, device performance metrics (e.g., battery level, error logs, etc.), or any other such data stored by the implantable device 400. As described in more detail below, the data communications unit 412 can utilize a variety of techniques to encrypt or otherwise obfuscate the data to maintain security during transmission to the interrogation device 450. The data communications unit 412 may also receive data from the interrogation device 450 (via the communications link 460). For example, the data communications unit 412 may receive instructions to obtain certain physiological measurements via the sensing elements 110, to emit a localization signal via the localization unit 410, or to perform other functions.

In some embodiments, the data communications unit 412 determines whether to emit a localization signal based on a characteristic of the interrogation device 450 that induces a current in the coil 408 of the implantable device 400. For example, the data communications unit 412 may assess a characteristic such as a field intensity threshold of electrical energy received from the interrogation device 450, a frequency of the electrical energy received from the interrogation device 450, etc. These characteristics can aid in discriminating between a trusted interrogation device (i.e. an interrogation device suitable for pairing) and a non-trusted interrogation device (i.e., an interrogation device unsuitable for pairing), such that only pre-authorized interrogation devices 450 are able to cause the data communications unit 412 to transmit data to the interrogation device 450.

In some embodiments, the implantable device 400 may also be in communication with the remote computing device(s) 470 over a wireless communications link (e.g., the Internet, public and private intranet, a local or extended Wi-Fi network, cell towers, etc.). The remote computing device(s) 470 can be, for example, server computers associated with a hospital, medical provider, medical records database, insurance company, or other entity charged with securely storing patient data and/or device data. In some embodiments, the obfuscated data provided by the data communications unit 412 can be de-obfuscated (e.g., unencrypted) at a remote location. In some embodiments, the implantable device 400 may be in direct communication only with the interrogation device 450, which in turn is in communication with remote computing device(s) 470.

The implantable device 400 can also include a reservoir 414 that is in fluid communication with an outlet port 416. In use, a needle 420 can be removably inserted into the fluid reservoir 414, and a catheter 430 can be fluidically coupled to the outlet port 416, thereby establishing a fluid path between the needle 420 and the catheter 430 for introduction of fluid (e.g., medication) or withdrawal of fluid (e.g., aspiration of blood for testing). In some embodiments, the implantable device 400 may omit the reservoir or outlet port, for example in the case of pacemakers, deep brain stimulators, or other implantable devices that do not require delivery or extraction of fluids. In some embodiments, the implantable device 400 may include other elements that serve additional functions—for example a pacemaker can include a pacemaking unit configured to deliver current to cardiac leads, etc.

As noted previously, the implantable device 400 is configured to communicate wirelessly with the interrogation device 450. The interrogation device 450 can be, for example, a special-purpose interrogation device, a smartphone (with or without associated accessory hardware such as a conductive coil), or other suitable computing device configured to communicate with the implantable device 400. The interrogation device 450 can include a power source 452 (e.g., a battery or wired connection for external power), a memory 454, and a processor 458. In some embodiments, the interrogation device 450 can also include a display 462 (e.g., an electronic screen) configured to display information visually to a user, and an input 464 (e.g., buttons, a touchscreen input, etc.) configured to receive user input.

As noted above, the interrogation device 450 also includes a coil 456 configured to inductively couple with the coil 408 of the implantable device. For example, when the implantable device 400 and the interrogation device 450 are placed in proximity to one another, an alternating current driven through the coil 456 of the interrogation device 450 creates an alternating magnetic field that, in turn, induces an electrical current in the coil 408 of the implantable device. This induced current in the coil 408 can be used to recharge the battery 402, cause the localization unit 410 to emit a localization signal, and/or to cause the data communications unit 412 to transmit data to or receive data from the interrogation device 450.

As also noted above, the interrogation device 450 includes a communications link 460 configured to communicate with the data communications unit 412 of the implantable device 400 and/or to communicate with the remote computing device(s) 470. The communications link 460 can include a wired connection (e.g., an Ethernet port, cable modem, FireWire cable, Lightning connector, USB port, etc.) or a wireless connection (e.g., including a Wi-Fi access point, Bluetooth transceiver, near-field communication (NFC) device, and/or wireless modem or cellular radio utilizing GSM, CDMA, 3G and/or 4G technologies).

As discussed previously, the interrogation device 450 can include a localization reader 466 that is configured to read, identify, or detect localization signals emitted via the localization unit 410 of the implantable device 400. In various embodiments, the localization reader 466 can include a light sensor or array, a microphone or array of microphones, a magnetic field probe (e.g., an array of Hall effect sensors), an antenna or other radiofrequency receiver, an ultrasound receiver, an electromagnetic sensor, a temperature sensor, or any other transducer or sensor configured to detect, identify, or read a localization signal emitted via the localization unit 410 of the implantable device 400.

Wireless Charging and Localization

As noted above, the advent of vascular access devices having on-board electronics requires a mechanism for powering such devices, and preferably for recharging a battery of such devices. Additionally, the on-board electronics may be used for localization, thereby obviating the need for bulky, protruding devices that are detectible via palpation of a patient's skin. As described in more detail below, an interrogation device that includes a coil can be used to wirelessly recharge an implanted vascular access device while also activating a localization signal. As a result, bringing an interrogation device into proximity with an implanted vascular access device causes the implanted vascular access device to be wirelessly recharged while emitting a localization signal that aids a clinician in correctly placing a needle into the fluid reservoir of the vascular access device.

FIGS. 5A-7B illustrate various embodiments of an interrogation device 450 for use with an implantable device 400 such as a vascular access device. The interrogation device 450 includes a housing 502 that defines a central aperture 504. In operation, the housing 502 can be placed against a patient's skin adjacent to the implantable device 400 such that the aperture 504 is substantially aligned with the device 400. A clinician may then hold the interrogation device 450 in position or adhere it to the patient's skin, followed by insertion of a needle through the patient's skin and into the device 400 as described previously with respect to FIG. 3.

Figure 5A:
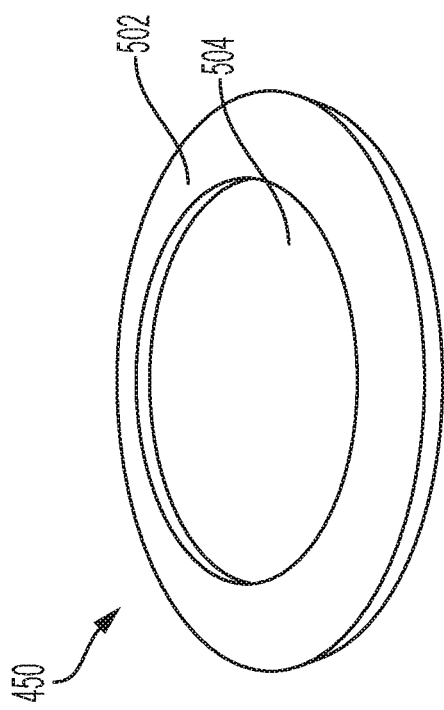
FIGS. 5A-5C illustrate example interrogation device geometries in accordance with the present technology.
Figure 5C:
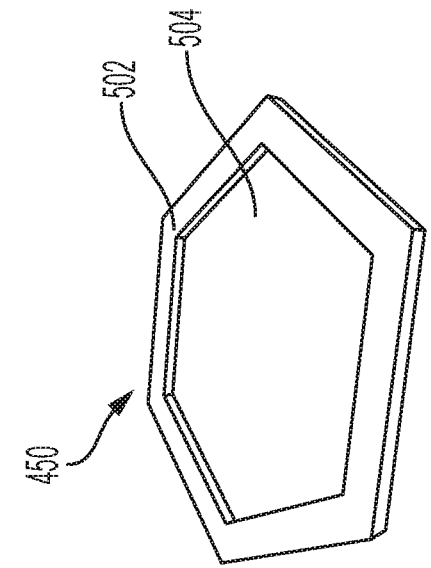
Figure 5B:
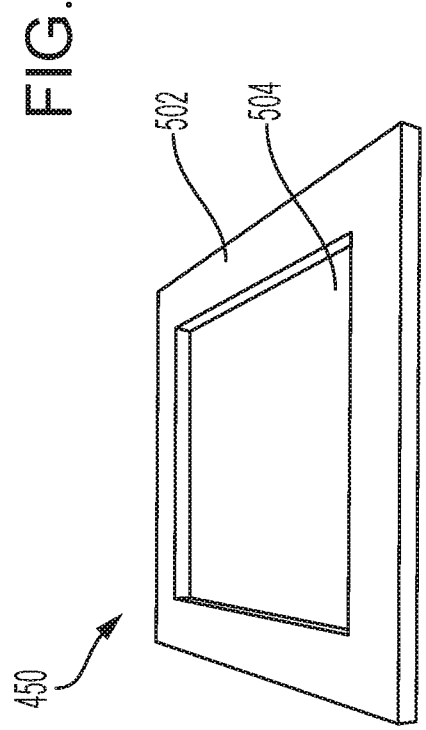

Referring to FIGS. 5A-5C, the housing 502 of the interrogation device 450 can assume a range of different geometries in various embodiments. For example, the housing 502 can define a substantially circular geometry, a rectangular or square geometry, a polygonal geometry, or any other shape that defines an aperture 504. The general shape of the interrogation device 450 facilitates both wireless charging of the implantable device 400 as well as access to the implantable device 400 using a medical needle. Accordingly, the housing 502 of the interrogation device 450 defines a generally flat geometric shape enclosing a wire or other electrically conductive structure and other associated electronic components. The housing 502 may be circular, ovoid, rectangular, polygonal, or any other irregular shape that is designed to conform to the body. In some embodiments, the interrogation device 450 is flexible to conform to the external contour of the patient's skin, but in at least some embodiments the interrogation device 450 is rigid or semi-rigid, for example being made of plastic or metal, or of a semi-rigid medical grade material like polyurethane polymers or silicone in order to protect the inner electrical components.

In some embodiments, the size and shape of the central aperture 504 is configured to aid the user in accurately targeting a reservoir 414 of an implantable medical device 400 with a needle. In one embodiment, this aperture 504 is small enough to act as a tunnel to physically guide the needle into the center of a reservoir 414 of the implantable medical device 400. For example, in some embodiments the aperture 504 may define an area having a size that is substantially similar to a cross-sectional size of the fluid reservoir 414. In some embodiments, the area defined by the aperture 504 is smaller than a cross-sectional size of the fluid reservoir 414. In another embodiment, the aperture 504 may be large enough to enable the user to access the reservoir 414 with a needle trajectory at least partially offset from the center axis of the reservoir 414.

Figure 6A:
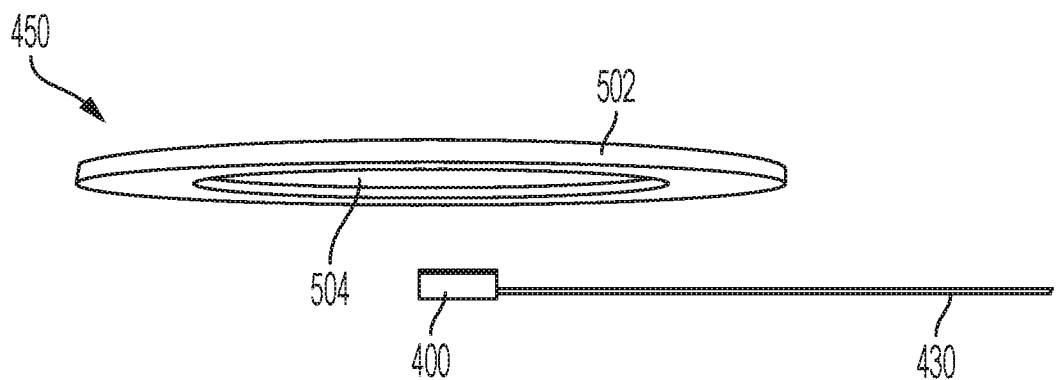
FIGS. 6A-6C illustrate a vascular access device positioned for wireless communication with an interrogation device in accordance with the present technology.
Figure 6B:
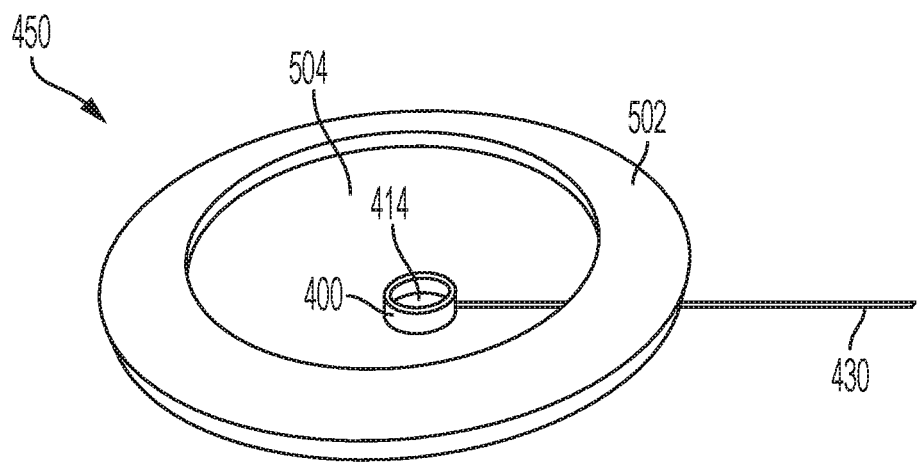
Figure 6C:
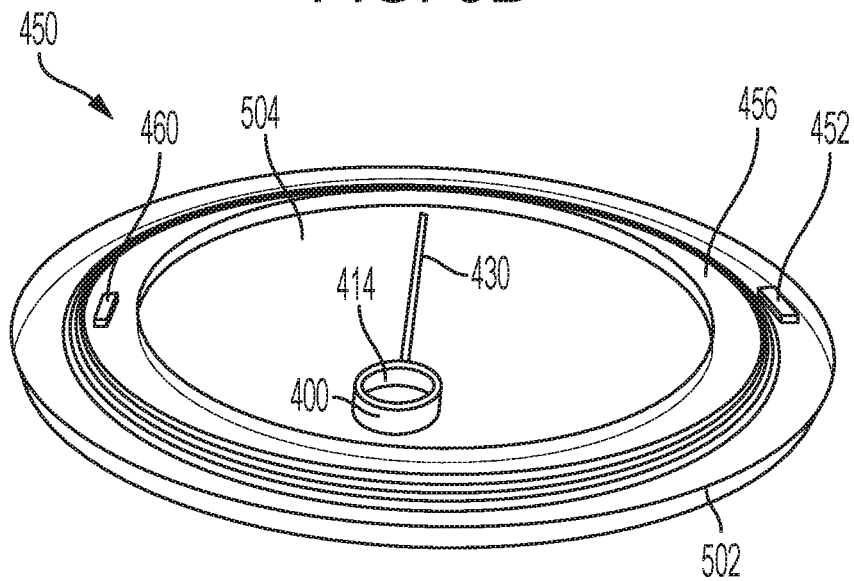

FIGS. 6A-6C illustrate the interrogation device 450 positioned in proximity to an implantable device 400. The device 400 includes a reservoir 414 fluidically coupled to a catheter 430. As best seen in FIG. 6C in which an upper portion of the housing 502 is removed, the housing 502 encloses the electronic components of the interrogation device 450, including the power source 452 (e.g., a battery or a connection for a wired power source), the communications link 460 (e.g. a wireless antenna and associated electronics), and the coil 456 that is electrically coupled to the power source 452. Although not illustrated here, in some embodiments the housing 502 may also contain a localization reader 466 or any other electronic components. When in use, the coil 456 (or other conductive material) can be driven with an alternating current, thereby inducing an alternating magnetic field within the central aperture 504 and aligned along an axis generally orthogonal to the patient's skin (i.e., generally orthogonal to the plane of the aperture 504). When positioned over the implanted medical device 400 having a coil of conducting material (e.g., coil 408), this alternating magnetic field induces an alternating electrical current within the coil 408 of the implantable device 400 which can be harvested for recharging a battery of the implantable device 400 or to perform other operations via the implantable device 400.

In addition to recharging a battery of the implantable device 400, the induced electrical current in the coil of the implantable device 400 may cause the implantable device 400 to emit a localization signal in response to the induced current. This remote activation of a localization signal allows for a smaller, lower profile design to the device that improves patient comfort and satisfaction with the device while still allowing for accurate cannulation of the device by a healthcare professional. As noted previously, the implantable device 400 can include a localization unit 410 configured to emit a localization signal in response to current induced via the interrogation device 450. The localization signal can take a number of different forms, including, for example, visual output (e.g., lights), sound, tactile stimuli, vibration, magnetic fields, electromagnetic emissions, radio-isotope decays, ultrasound, or any other means of localization that does not require palpation of the port device in its resting state. In one example, a plurality of LEDs are positioned around the reservoir 414 of the implantable device 400. In response to the induced current from the interrogation device 450, the LEDs emit light that transilluminates the patient's skin, allowing a clinician to localize the implantable device 400.

Figure 7A:
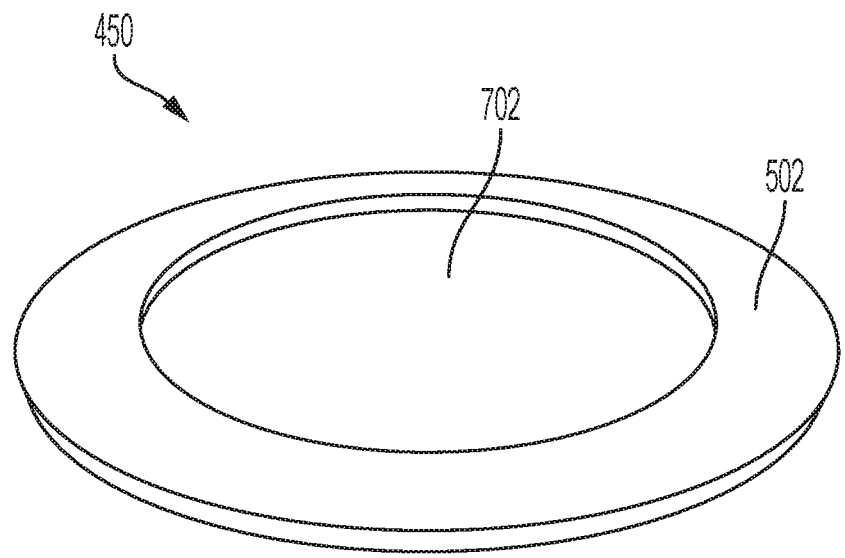
FIGS. 7A and 7B illustrate an additional example of an interrogation device in accordance with the present technology.
Figure 7B:
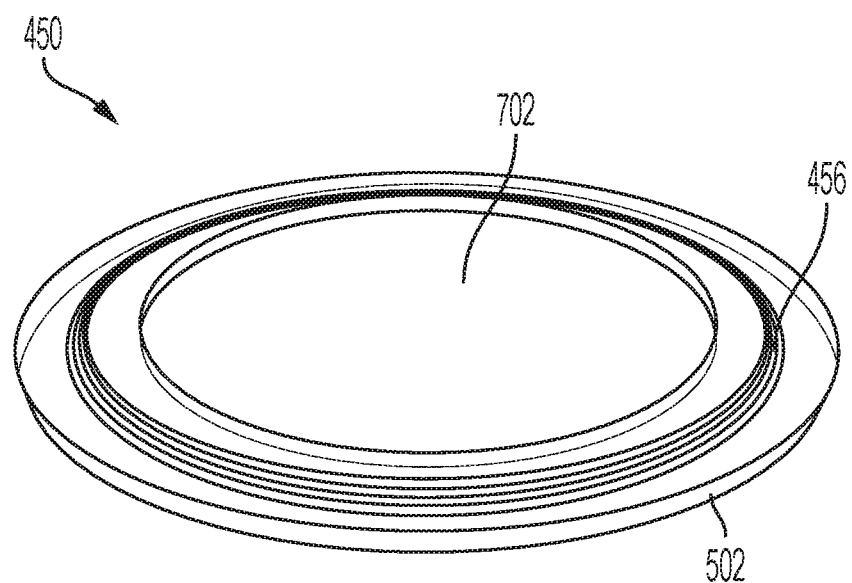

FIGS. 7A and 7B illustrate another embodiment of the interrogation device 450 in which a membrane 702 extends over the aperture 504 defined by the housing 502. The membrane 702 can be, for example, an adhesive material such that the interrogation device 702 can be adhered to a patient's skin. In some embodiments, the membrane 702 is a translucent or transparent medical adhesive such as TEGADERM. In some embodiments, the membrane 702 can be impregnated with therapeutic agents, for example an antimicrobial agent such as chlorhexidine, assisting with maintaining sterility of the procedure and preventing colonization of the implantable device 400 with infectious agents such as bacteria or fungi.

The addition of an adhesive material can aid a clinician in administering therapy via the implantable device 400. For example, in instances in which the implantable device 400 is low profile, it may be difficult or impossible to localize via palpation, and accordingly additional means of localization may be required. The clinician, knowing the general anatomic location of the implantable device 400, may place the interrogation device 450 over that anatomic region. Through inductive activation and power, the implantable device 400 may emit a localization signal, for example by activating a single or an array of LEDs that transilluminate through the skin, alerting the clinician of the precise location of the implantable device 400. The clinician may then place the interrogation device 450 on the skin of the patient with the central aperture 504 directly over the implantable device 400 so that the LEDs are still visualized (or other localization signal is detected). The interrogation device 450 may rest on the skin of the patient. If a membrane 702 includes an adhesive, the adhesive may secure the interrogation device 450 in position on the skin of the patient.

With the interrogation device 450 resting on or adherent to the patient's skin, the clinician is free to use two hands for the access procedure. Through the central aperture 504, the clinician may first sterilize the area of skin using a topical antiseptic such as chlorhexidine. Once the region is sterilized, using gloved hands, the clinician inserts a non-coring Huber type needle into the implantable device 400 using the LEDs as a visual guide for accurate needle placement (or using another suitable localization signal as a means for identifying the precise location of the reservoir for accurate needle placement). Using dressings, tape, or other adhesives such as TEGADERM, the needle is secured in place, attached to syringes or IV tubing, and then used for either aspiration of blood or infusion of therapeutic agents. For ease of use, all the components required for the access procedure including the interrogation device 450 may be packaged together in a single-use kit. In embodiments in which an adhesive such as TEGADERM covers at least a portion of the aperture 504 of the device 450, the clinician may advance the needle through the adhesive to reach the implantable device 400.

Figure 8A:
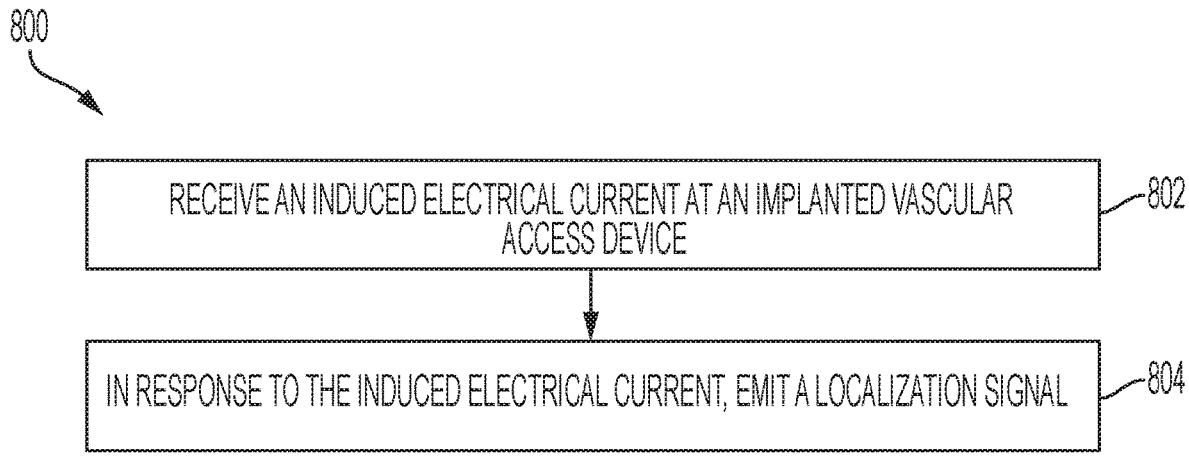
FIGS. 8A and 8B are flow diagrams illustrating methods of localizing an implanted vascular access device in accordance with the present technology.
Figure 8B:
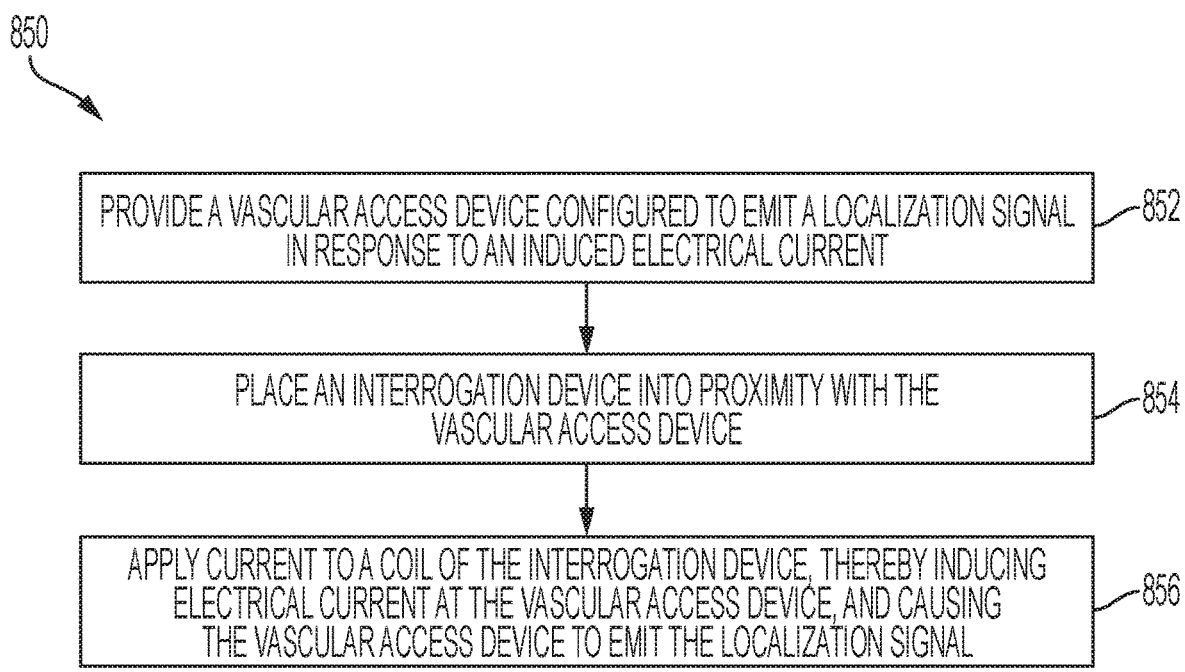

FIGS. 8A and 8B are flow diagrams illustrating methods of localizing an implanted vascular access device in accordance with the present technology. With respect to FIG. 8A, the method 800 begins in block 802 with receiving an induced electrical current at an implanted vascular access device 400. For example, the implantable device 400 can receive an induced current as a response to placing the interrogation device 450 into proximity with the implantable device 400 and supplying alternating current to the coil 456 of the interrogation device 450. The method 800 proceeds in block 804 with emitting a localization signal in response to the induced electrical current. In some embodiments, the induced electrical current is sufficient to fully power the emission of the localization signal (e.g., via the localization unit 410 of the implantable device 400). In some embodiments, the vascular access device has no on-board battery, and the localization signal is powered entirely via the induced electrical current from an external device such as the interrogation device 450. In other embodiments, the induced electrical current operates as a control signal to initiate emission of the localization signal, but the localization unit 410 draws additional power from the battery 402 in order to emit the localization signal.

As noted previously, the localization signal can take a variety of forms. For example, the localization signal can be light emitted from one or more light sources, sound emitted from one or more speakers, ultrasound emitted from one or more transducers, vibration or movement caused by one or more actuators, electromagnetic radiation, data transmission, heat emitted from a heating element, a magnetic field generated by one or more magnets, radiation emitted from a decaying radioisotope, or any other suitable signal that aids a clinician and/or an interrogation device 450 in localizing an implantable device 400.

Turning now to FIG. 8B, the method 850 begins in block 852 with providing a vascular access device configured to emit a localization signal in response to an induced electrical current. For example, the implantable medical device 400 can be positioned beneath a patient's skin at a target site, such as within the patient's chest. In block 854, the method 850 continues with placing an interrogation device into proximity with the vascular access device. For example, the interrogation device 450 can be positioned over the patient's skin and substantially aligned with the implanted medical device 400. In block 856, alternating electrical current is applied to a coil of the interrogation device, thereby inducing electrical current at the vascular access device. This causes the vascular access device to emit the localization signal as described previously.

Data Communication and Security

While remote patient monitoring via an electronically equipped implantable device 400 provides many benefits to patients and clinicians, the risks to data security, privacy, and security of device operation all pose serious threats to safe and effective operation of such a device. Accordingly, the present technology provides a number of techniques for securely storing, transmitting, and receiving patient data, device data, control instructions, and any other sensitive information sent between an implantable device 400 and one or more external devices. The external devices can include an interrogation device 450 for local communication (e.g., near-field communication (NFC), infrared wireless, Bluetooth, ZigBee, Wi-Fi, inductive coupling, or capacitive coupling) and/or remote computing devices accessed over a network connection (e.g., an intranet, the Internet, etc.). The secure communication techniques described herein enable protection of private patient information and ensures protection from remote hacking and take-over of device operation.

Figure 9A:
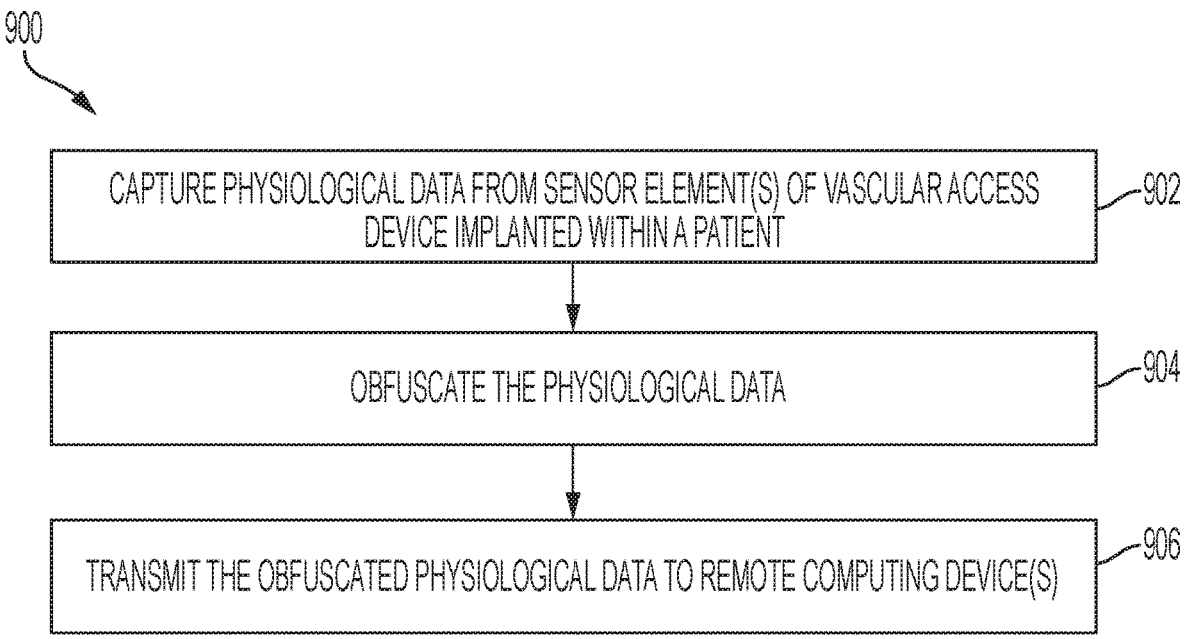
FIGS. 9A and 9B are flow diagrams illustrating methods of data communication between an implanted vascular access device and one or more remote computing devices.
Figure 9B:
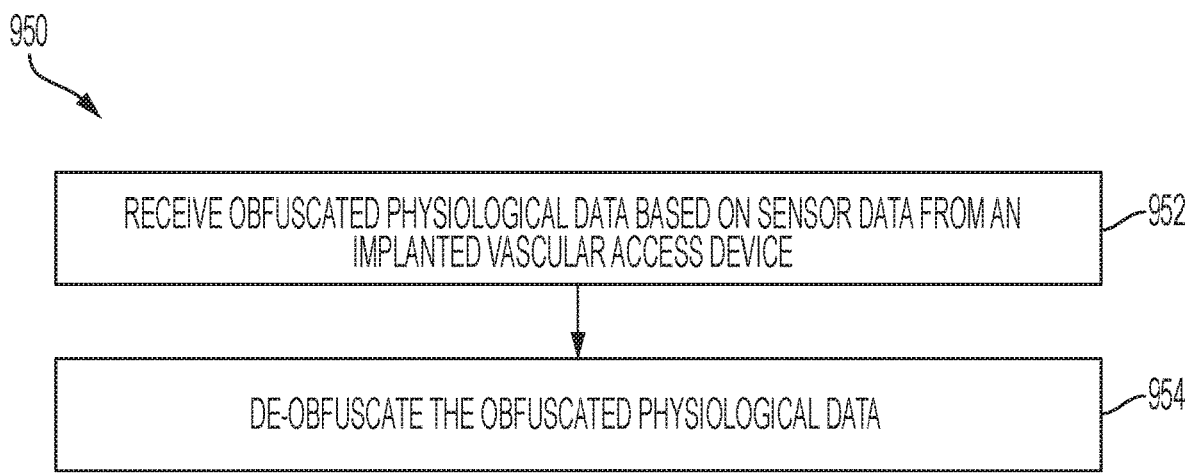

FIGS. 9A and 9B are flow diagrams illustrating methods of data communication between an implanted vascular access device such as the implantable device 400 and one or more remote computing devices (e.g., interrogation device 450 or remote computing device(s) 470). Referring to FIG. 9A, the method 900 begins with capturing physiological data from sensor elements 110 of a vascular access device 400 implanted within a patient. As noted above, the physiological data can include a wide variety of different measures or parameters, including, for example, heart rate, temperature, blood pressure (e.g., systolic blood pressure, diastolic blood pressure, mean blood pressure), blood flow rate, blood velocity, pulse wave speed, volumetric flow rate, reflected pressure wave amplitude, augmentation index, flow reserve, resistance reserve, resistive index, capacitance reserve, hematocrit, heart rhythm, electrocardiogram (ECG) tracings, body fat percentage, activity level, body movement, falls, gait analysis, seizure activity, blood glucose levels, drug/medication levels, blood gas constituents and blood gas levels (e.g., oxygen, carbon dioxide, etc.), lactate levels, hormone levels (such as cortisol, thyroid hormone (T4, T3, free T4, free T3), TSH, ACTH, parathyroid hormone), and/or any correlates and/or derivatives of the foregoing measurements and parameters (e.g., raw data values, including voltages and/or other directly measured values).

The method 900 continues in block 904 with obfuscating the physiological data, and in block 906, the obfuscated physiological data is transmitted to the remote computing device(s). As described in more detail below, this obfuscation can take a number of different forms. This obfuscation can include, for example, encrypting data, parsing encrypted data into packets, and re-ordering the encrypted data packets, anonymizing data, use of blockchain technologies, or other methods for rendering communications unintelligible to anyone other than the intended recipient.

Referring now to FIG. 9B, the method 950 includes receiving obfuscated physiological data based on sensor data from an implanted vascular access device. For example, the interrogation device 450 or a remote computing device 470 may receive the obfuscated physiological data from the implantable device 400. This may be received over short-range wireless communication in the case of the interrogation device 450, or a network communication in the case of the remote computing device(s) 470. The method 900 continues in block 954 with de-obfuscating the obfuscated physiological data. As described below, in some embodiments the recipient device (e.g., the interrogation device 450 or the remote computing device 470) utilizes algorithms and techniques to de-obfuscate the data in a manner that maintains the unintelligibility and inaccessibility of the obfuscated data to any persons or entities who intercept the obfuscated data during transmission between the implantable device 400 and the recipient device.

In one example, industry-standard algorithms (e.g., symmetric or asymmetric-key encryption) are used to encrypt the data via the data communications unit 412 of the implantable device 400. The encrypted data may then be parsed into component parts such that the component packets are individually unintelligible. These components parts may then be assembled into a data stream and sent according to a scheme known only to the intended recipient. In at least some embodiments, unencrypted data may be parsed into component parts and sent according to a predetermined scheme. In some embodiments, the component parts may be separately encrypted after having been parsed into separate parts.

Data can be parsed in many ways. For example, data can be separated into individualized packets and compiled into a stream interspersed with filler data packets (e.g., packets that contain non-physiological data, random data, or other suitable filler data). In this scheme, the recipient may be provided with a key for identifying the filler data packets within the data stream. For example, the pattern of filler packets could be predetermined. For example, a reconstructed data stream may be as follows: 1 Kb data, 0.1 Kb filler, 1 Kb data, 0.3 Kb filler, 1 Kb data, 0.8 Kb filler. This pattern might be identified as 0.1-0.3-0.8 for decryption purposes, indicating sequence of data sizes for the filler packets. Filler packet sizes could also be defined by predetermined sequences, e.g. Fibonacci sequence or other patterned sequence. In some embodiments, data stream filler packet size patterns are used to encode start and stop points in the stream, analogous to the start and stop transcription instructions encoded in DNA for biologic systems. For example, when a sequence of packets has a file size pattern that matches a predetermined "code," the recipient may identify the sequence as an instruction to start decrypting subsequent data packets or to take other action. Filler packet size or filler packet size sequence may also be used to communicate meta instructions, such as start reading, stop reading, skip to, change send/receive algorithm, overwrite existing data, system reset, revert to factory settings, pair with new device, change duty cycle, shutdown, etc.

In some embodiments, data is encrypted and divided into component packets. These packets are then re-ordered and assembled into a data stream for transmission. In some embodiments, the recipient may have prior knowledge of the re-ordering scheme (e.g. 1st 1 Kb, 3rd 1 Kb, 2nd 1 Kb, etc.). In some embodiments, data is encrypted and divided into incomplete blocks of unintelligible information and sent at time-delayed intervals with the recipient having prior knowledge of the time-delay sequence required for reconstruction of the encrypted data packets. In some embodiments, this re-ordering scheme may be used without initial encryption of the underlying data, as eavesdropping systems would likely either miss necessary portions of the data stream because of time delays or such eavesdropping systems would not be able to interpret the data stream because the data packets would have no identifying markers or patterns for reconstruction. Depending on device use requirements, time delays could be as short as picoseconds or as long as weeks. This transmission delay may be protective, especially with an implantable device, because the patient moves around her home and town throughout the day and week; so it becomes increasingly unlikely that an eavesdropping observing device or system would be in close enough proximity to receive enough of the data stream to reconstruct it, even if the observer knew the time delay algorithm.

As the transmitted data is being sent from an implantable device 400, timing of data transmission may also be driven by the physical or physiologic state of the patient. For example, it may be advantageous to send data only while the patient is in a specific physical state like running, standing still, sleeping, or while the patient is experiencing a special physiologic event like low blood sugar, low oxygen saturation, low blood cell counts. In the former case, data transmission security is improved at least in part due to the unpredictable behavior of the patient, and transmission can also be controlled by the patient in this way. For example, the patient may choose to run for a few minutes to initiate data transmission, and in embodiments relying on short-range communication (e.g., Bluetooth low energy has a transmission range of approximately 30 feet) the patient's movement would enhance security by taking her out of range of any nearby eavesdropping devices. In some embodiments, physiologically-triggered data transmission can serve as an additional patient safety measure or emergency alert, for example by transmitting a full set of patient data if the patient experiences a diabetic, asthmatic, or trauma event as detected by the onboard sensing elements of the implantable device 400.

In some embodiments, additional data obfuscation can be achieved by scattering incomplete blocks of unintelligible information through internet-based blockchain registries (e.g., Ethereum). In doing so, data could be retrieved by a remote receiver and interpreted based on a predetermined scheme or algorithmically derived interpretation methodology. In some embodiments, the component packets can be sent to different remote computing devices sequentially or in parallel. These component packets may then later be re-transmitted to a central computing device or group of computing devices for re-assembly and decryption.

To manage interpretation of data parsing schemes and data stream reconstruction, paired devices may use authentication software or authentication codes at the beginning and end of parsed data packets. In some embodiments, artificial intelligence may be employed for the sending device to autonomously create new data parsing schemes and to teach the receiving device how to interpret the schemes for incoming data. In this way, through repeated back-and-forth communication, the paired sender and receiver can evolve a unique language, or "slang" form of communication, known only to these paired devices, thereby making each successive communication more obscure and more difficult for a non-paired device, reader, system, or observer to interpret. For example, in such a scheme, the transmitting device may obfuscate physiological data according to a first technique (e.g., using interspersed filler packets according to a first pattern) and send the obfuscated data to a remote computing device. Subsequently, the transmitting device may obfuscate further physiological data according to a second technique different from the first (e.g., using interspersed filler packets according to a second pattern) and send the obfuscated data to the remote computing device for de-obfuscation. By varying the obfuscation techniques over time, the difficulty for an intercepting party (e.g., an entity using a man-in-the-middle attack) to decipher the obfuscated data.

An example of an autonomously evolving communication security system involves an implantable device 400 and an interrogation device 450. The two devices may be programmed with the same initial communication obfuscation scheme. The process of pairing the implantable device 400 and the interrogation device 450 includes instructions for the two devices to begin autonomous evolution of their communication scheme (e.g., by evolving the pattern of filler packets, the time-delay sequence, or other such parameter of an obfuscation scheme). Communication evolution may be programmed to iterate quickly in order for the paired devices to quickly distinguish their language from any other devices. In one embodiment, the paired devices also retain their "native" originating language for communication with non-paired devices. In some embodiments, the paired devices do not retain their original language, making it impossible for non-paired devices to communicate with them. In this embodiment, the paired devices could be reprogrammed only by performing a hard reset, erasing all data and data communication schemes. The data erasure upon reset would serve as an added security measure. However, in alternative embodiments, the device may be reset without erasing the data communication scheme and/or without erasing the stored data. This embodiment may facilitate initial device research and development and use of paired devices when lower level security is acceptable.

In some embodiments, secure data transmission is achieved through a direct wireless connection between the implantable device 400 and the interrogation device 450 such as inductive coupling. This very short-range communication is far less likely to be intercepted by unintended recipients than, for example, Bluetooth communications which have a much longer range. In this embodiment, the coil 408 of the implantable device 400 is inductively coupled with the coil 456 of the interrogation device, allowing the two to communicate via very short-range direct wireless communication. In this embodiment, data may be encoded to the alternating current driving the coil 408 of the implantable device 400 utilizing amplitude modulation and/or frequency modulation schemes.

CONCLUSION

Although many of the embodiments are described above with respect to systems, devices, and methods for wireless charging, localization, and data communications for vascular access devices, the technology is applicable to other applications and/or other approaches, such as other types of implantable medical devices (e.g., pacemakers, implantable cardioverter/defibrillators (ICD), deep brain stimulators, insulin pumps, orthopedic devices, and monitoring devices such as pulmonary artery pressure monitors). Additionally, the present technology may be applied to other wireless charging, localization, or secure data communications techniques. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1-9B.

The above detailed descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Where a range of values is provided, it is understood that each intervening value, to the tenth of the unit of the lower limit unless the context clearly dictates otherwise, to between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

The invention claimed is:

1. An implantable vascular access device comprising:
   a fluid reservoir;
   a self-sealing cover disposed over the reservoir;
   an outlet port configured to mate with a catheter, the outlet port fluidically coupled to the fluid reservoir;
   one or more sensors configured to capture physiological data while the device is implanted within a patient; and
   a data communications processor configured to:
     receive physiological data from the one or more sensors;
     obfuscate the physiological data including:
       encrypting the physiological data through at least one of symmetric and asymmetric-key encryption;
       parsing the encrypted physiological data into component packets; and
       arranging the component packets into a data stream interspersed with filler packets containing non-physiological data; and
     transmit the data stream to one or more remote computing devices.

2. The device of claim 1, wherein the component packets are individually unintelligible.

3. The device claim 1, wherein the filler packets have a predetermined data size.

4. The device of claim 1, wherein the filler packets are interspersed into the data stream according to a predetermined pattern.

5. The device of claim 1, wherein obfuscating the physiological data further comprises:
   after parsing the encrypted data into component packets, re-ordering the component packets; and
   arranging the re-ordered component packets into a data stream,
   wherein transmitting the obfuscated physiological data comprises transmitting the data stream to one or more remote computing devices.

6. The device of claim 1, wherein transmitting the obfuscated physiological data to one or more remote computing devices comprises transmitting a first packet at a first time and, after a predetermined time delay, transmitting a second packet at a second time.

7. The device of claim 6, wherein the predetermined time delay is at least one of at least 60 seconds, at least 10 minutes, or at least one hour.

8. The device of claim 6, wherein the predetermined time delay corresponds to a predetermined pattern for transmission of subsequent packets.

9. The device of claim 1, wherein the data communications processor is configured to transmit a first of the packets to a first remote computing device and to transmit a second of the packets to a second remote computing device, different from the first remote computing device.

10. The device of claim 1, wherein the data communications processor is configured to:
    obfuscate the physiological data according to a first technique, the first technique including at least:
      encrypting the physiological data through at least one of symmetric and asymmetric-key encryption;
      parsing the encrypted physiological data into component packets; and
      arranging the component packets into a data stream interspersed with filler packets containing non-physiological data in a first pattern;
    transmit the obfuscated physiological data to one or more remote computing devices;
    receive a response from the one or more remote computing devices;
    receive additional physiological data from the one or more sensors; and
    based on the response from the one or more remote computing devices, obfuscate the physiological data according to a second technique, different from the first technique, wherein obfuscating the physiological data according the second technique comprises:
      encrypting the physiological data through at least one of symmetric and asymmetric-key encryption;
      parsing the encrypted physiological data into component packets; and
      arranging the component packets into a data stream interspersed with filler packets containing non-physiological data in a second pattern, the second pattern different from the first pattern.

11. The device of claim 1, wherein the one or more remote computing devices is associated with a blockchain network.

12. The device of claim 1, wherein the data communications processor is configured to transmit the obfuscated physiological data to one or more remote computing devices via short-range wireless transmission.

13. The device of claim 12, wherein the short-range wireless transmission comprises one or more of: near-field communication (NFC), infrared wireless, Bluetooth, Zig-Bee, Wi-Fi, inductive coupling, or capacitive coupling.

14. The device of claim 1, further comprising a conductive coil, wherein transmitting the obfuscated physiological data to one or more remote computing devices comprises:
    encoding the obfuscated physiological data via frequency modulation and/or amplitude modulation; and
    driving the coil with electrical energy corresponding to the encoded data, thereby transmitting the encoded data to an inductively coupled remote computing device.

15. The device of claim 1, wherein the sensors comprise one or more of: EKG sensors, a temperature sensor, an accelerometer, a gyroscope, a magnetometer, a pulse oximeter, a pressure sensor, a light sensor, a pH sensor, a blood-gas sensor, or a blood-chemistry sensor.

16. The device of claim 1, wherein the physiological data comprises one or more of: an EKG reading, a pulse rate, a blood pressure, a temperature, detected-motion data, a blood oxygenation, pH data, or blood-constituent data.

17. The device of claim 1, further comprising a catheter fluidically coupled to the output port.

\* \* \* \* \*